US009669036B2

(12) United States Patent
Roizman et al.

(10) Patent No.: US 9,669,036 B2
(45) Date of Patent: Jun. 6, 2017

(54) MODULATION OF REACTIVATION OF A LATENT VIRUS

(71) Applicant: THE UNIVERSITY OF CHICAGO, Chicago, IL (US)

(72) Inventors: Bernard Roizman, Chicago, IL (US); Guoying Zhou, Madison, WI (US); Te Du, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 14/891,200

(22) PCT Filed: May 14, 2014

(86) PCT No.: PCT/US2014/000110
§ 371 (c)(1),
(2) Date: Nov. 13, 2015

(87) PCT Pub. No.: WO2014/185973
PCT Pub. Date: Nov. 20, 2014

(65) Prior Publication Data
US 2016/0089376 A1    Mar. 31, 2016

Related U.S. Application Data

(60) Provisional application No. 61/823,355, filed on May 14, 2013.

(51) Int. Cl.
*A61K 31/5377* (2006.01)
*A61K 31/12* (2006.01)
*A61K 31/165* (2006.01)
*A61K 31/167* (2006.01)
*A61K 45/06* (2006.01)
*A61K 31/255* (2006.01)
*A61K 31/40* (2006.01)
*A61K 31/4192* (2006.01)
*A61K 31/4402* (2006.01)
*A61K 31/185* (2006.01)
*A61K 31/4045* (2006.01)
*A61K 31/436* (2006.01)
*A61K 31/4375* (2006.01)
*A61K 31/4406* (2006.01)
*A61K 31/4745* (2006.01)
*A61K 31/517* (2006.01)

(52) U.S. Cl.
CPC .......... *A61K 31/5377* (2013.01); *A61K 31/12* (2013.01); *A61K 31/165* (2013.01); *A61K 31/167* (2013.01); *A61K 31/185* (2013.01); *A61K 31/255* (2013.01); *A61K 31/40* (2013.01); *A61K 31/4045* (2013.01); *A61K 31/4192* (2013.01); *A61K 31/436* (2013.01); *A61K 31/4375* (2013.01); *A61K 31/4402* (2013.01); *A61K 31/4406* (2013.01); *A61K 31/4745* (2013.01); *A61K 31/517* (2013.01); *A61K 45/06* (2013.01)

(58) Field of Classification Search
CPC ..... A61K 31/5377; A61K 45/06; A61K 31/12
USPC ...................................... 514/234.2
See application file for complete search history.

(56) References Cited

U.S. PATENT DOCUMENTS 6,677,302 B2 * 1/2004 Faller .................... A61K 45/06
424/184.1
2010/0291067 A1   11/2010 Planelles et al.

FOREIGN PATENT DOCUMENTS

WO    WO-2012/0139068 A2   10/2012

OTHER PUBLICATIONS

Horig et al. Journal of Translational Medicine 2004, 2(44), p. 1-8.*
Schafer et al. Drug Discovery Today, 2008, 13 (21/22), 913-916.*
Sen et al. PNAS, (2012), 109(2), p. 600-605.*
Al-Dujaili et al., "Ocular Herpes Simplex Virus: How are Latency, Reactivation, Recurrent Disease and Therapy Interrelated?" Future Microbiol, 6(8):877-907 (2011).
Balasubramanyam et al., "Curcumin, a Novel p300/CREB-Binding Protein-Specific Inhibitor of Acetyltransferase, Represses the Acetylation of Histone,Nonhistone Proteins and Histone Acetyltransferase-Dependent Chromatin Transcription," J Biol Chem 279(49): 51163-51171 (2004).
Balasubramanyam et al., "Small Molecule Modulators of Histone Acetyltransferase p300," J Biol Chem 278: 19134-19140 (2003).
Chang, et al. "Inhibition of Epstein-Barr Virus Lytic Cycle by (-)-Epigallocathechin Gallate," Biochem Biophys Res Comm 301:1062-1068 (2003).
Choi, et al. "Epigallocatechin-3-Gallate, A Histone Acetyltransferase Inhibitor, Inhibits EBV-Induced B Lymphocyte Transformation Via Suppression of RelA Acetylation," Cancer Res. 69(2):583-592 (2009).
Cui et al., "Prediction and Identification of Herpes Simplex Virus 1-Encoded MicroRNAs," J Virol 80(11): 5499-5508 (2006).
Dannaher, et al. "Histone Deacetylase Inhibitors Induce Reactivation of Herpes Simplex Virus Type 1 in a Latency-Associated Transcript (LAT)-Independent Manner in Neuronal Cells," J Neurovirol. 11(3):306-317 (2005).
Du et al., "Modulation of Reactivation of Latent Herpes Simplex Virus 1 in Ganglionic Organ Cultures by p300/CBP and STAT3," Proc . Natl. Acad. Sci. (U S A) 110(28): E2621-E2628 (2013).

(Continued)

Primary Examiner — Yong Chu
(74) Attorney, Agent, or Firm — Marshall, Gerstein & Borun LLP

(57) ABSTRACT

The disclosure relates to methods of controlling the state of a virus (lytic or lysogenic) in an individual, such as a method of reactivating a latent virus in an individual, comprising administering one or more agents that modulates the activity of signal transducer and activator of transcription 3 (STAT3) or any of p300, CBP or p300/CBP. Also contemplated are methods further comprising administering an HDAC modulating agent, such as an HDAC inhibiting agent or an HDAC activating agent.

11 Claims, 20 Drawing Sheets

(56) References Cited

OTHER PUBLICATIONS

Du et al., "Disruption of HDAC/CoREST/REST Repressor by dnREST Reduces Genome Silencing and Increases Virulence of Herpes Simplex Virus," Proc Natl Acad Sci U S A 107(36):15904-15909 (2010).

Du et al., "HSV-1 Gene Expression from Reactivated Ganglia is Disordered and Concurrent with Suppression of Latency-Associated Transcript and miRNAs," Proc Natl Acad Sci U S A 108(46):18820-18824 (2011).

Du et al., "Induction of Apoptosis Accelerates Reactivation of Latent HSV-1 in Ganglionic Organ Cultures and Replication in Cell Cultures," Proc Natl Acad Sci U S A 109(36):14616-14621 (2012).

Farooq et al., "Herpes Simplex Epithelial and Stromal Keratitis: An Epidemiologic Update," Surv Ophthalmol 57(5):448-62 (2012).

Farrell et al., "Herpes Simplex Virus Latency-Associated Transcript is a Stable Intron," Proc Natl Acad Sci U S A, 88:790-794 (1991).

Gaub, et al. "HDAC Inhibition Promotes Neuronal Outgrowth and Counteracts Growth Cone Collapse Through CBP/p300 and P/CAF-dependent p53 Acetylation," Cell Death Differ, 17(9):1392-1408 (2010).

Gu et al., "Herpes Simplex Virus-Infected Cell Protein 0 Blocks the Silencing of Viral DNA by Dissociating Histone Deacetylases from the CoREST-REST Complex," Proc Natl Acad Sci U S A 104(43):17134-17139 (2007).

Held et al., "Control of HSV-1 latency in human trigeminal ganglia—current overview," J Neurovirol 17: 518-27 (2011).

International Search Report and Written Opinion from PCT/US2014/00110 dated Nov. 28, 2014.

International Preliminary Report on Patentability from PCT/US2014/00110 dated Nov. 26, 2015.

Kazantsev et al., "Therapeutic application of histone deacetylase inhibitors for central nervous system disorders," Nat Rev Drug Discov 7:854-68 (2008).

Khan et al., "Determination of the Class and Isoform Selectivity of Small-Molecule Hlstone Deacetylase Inhibitors," Biochem J 409:581-589 (2008).

Knipe et al., "Snapshots: Chromatin Control of Viral Infection," Virology 435:141-56 (2013).

Koeller, et al. "Chemical Genetic Modifier Screens: Small Molecular Trichostatin Suppressors as Probes of Intracellular Histone and Tubulin Acetylation," Chem Biol. 10:397-410 (2003).

Kriesel, et al. "Neuronal Reactivation of Herpes Simplex Virus May Involve Interleukin-6," J Neuroviron 3:441-448 (1997).

Mitchell et al., "Mapping of Low Abundance Latency-Associated RNA in the Trigeminal Ganglia of Mice Latently Infected with Herpes Simplex Virus Type 1," J. Gen. Virol. 71:125-132 (1990).

Morissette et al., "Herpesviruses and Chromosomal Integration," J. Virol. 84:12100-12109 (2010).

Munson et al., "A novel miRNA produced during lytic HSV-1 infection is important for efficient replication in tissue culture," Arch Virol 157: 1677-88 (2012).

Muylaert et al., "Replication and Recombination of Herpes Simplex Virus DNA," J. Biol. Chem. 286(18): 15619-15624 (2011).

Nebbioso et al., "Selective Class II HDAC Inhibitors Impair Myogenesis by Modulating the Stability and Activity of HDAC-MEF2 Complexes," EMBO Rep 10:776-82 (2009).

Perng et al., "Towards an Understanding of the Herpes Simplex Virus Type 1 Latency-Reactivation Cycle," Interdiscip Perspect Infect Dis 2010:1-18 (2010).

Proenca et al., "An Investigation of Herpes Simplex Virus Promoter Activity Compatible with Latency Establishment Reveals VP16-Independent Activiation of Immediate-Early Promoters in Sensory Neurones," J Gen Virol 92:2575-2585 (2011).

Roizman et al., "An Inquiry into the Mechanisms of Herpes Simplex Virus Latency," Annu Rev Microbiol 41: 543-71 (1987).

Roizman et al., "The First 30 Minutes in the Life of a Virus," Cell Cycle 4(8):1019-1021 (2005).

Roizman et al., Chapter 60—Herpes simplex viruses. in: Knipe, D.M., Howley, P.M. (Eds.), Fields Virology, sixth ed. 2013. Lippincott Williams & Wilkins, Philadelphia.

Roizman et al., "Checkpoints in productive and latent infections with herpes simplex virus 1: conceptualization of the issues," J Neurovirol 17: 512-7 (2011).

Siddiquee et al., "Selective Chemical Probe Inhibitor of Stat3, Identified Through Structure-Based Virtual Screening, Induces Antitumor Activity," Proc Natl Acad Sci U S A 104(18):7391-7396 (2007).

Spivack et al., "Identification of a Novel Latency-Specific Splice Donor Signal within the Herpes Simplex Virus Type 1 2.0-Kilobase Latency-Associated Transcript (LAT): Translation Inhibition of LAT Open Reading Frames by the Intron within the 2.0-Kilobase LAT," J Virol 65(12):6800-6810 (1991).

Steiner, "Herpes simplex virus encephalitis: new infection or reactivation?" Curr Opin Neurol 24: 268-74 (2011).

Takahashi et al., "Induction of Pluripotent Stem Cells from Mouse Embryonic and Adult Fibroblast Cultures by Defined Factors," Cell 126:663-76 (2006).

Umbach et al., "MicroRNAs expressed by herpes simplex virus 1 during latent infection regulate viral mRNAs," Nature 454:780-783 (2008).

Zhou et al., "HSV carrying WT REST establishes latency but reactivates only if the synthesis of REST is suppressed," Proc Natl Acad Sci U S A 110:E498-506 (2013).

\* cited by examiner

MK-2206: Akt inhibitor (250, 25, 2.5 nM)

GDC0941: PI3K inhibitor (1000, 100, 10nM)

Tofacitinib: Jak3 inhibitor (100, 10, 1nM)

BEZ-235: PI3K/mTOR inhibitor (400, 40, 4nM)

AMI-1: HMT inhibitor (1000, 100, 10nM)

Romidepsin: HDAC 1,2,4 and 6 inhibitor

Panobinostat: HDAC 1,2,3, 4, 5, 6,7,9 inhibitor

UNC0638: HMT inhibitor

Rapamycin: mTOR inhibitor

MODULATION OF REACTIVATION OF A LATENT VIRUS

CROSS REFERENCE TO RELATED APPLICATIONS

This application is a U.S. national phase entry pursuant to 35 U.S.C. §371 of International Patent Application No. PCT/US 14/00110, filed May 14, 2014, and claims the priority benefit under 35 U.S.C. §119(e) of U.S. Provisional Patent Application No. 61/823,355, filed May 14, 2013, the disclosure of which is incorporated herein by reference in its entirety.

STATEMENT OF GOVERNMENT INTEREST

This invention was made with government support under Grant Number R37CA078766, awarded by the National Institutes of Health (NIH). The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 47741A_SeqListing.txt; 1,385 bytes ASCII text file; created May 14, 2014.

FIELD OF THE INVENTION

The disclosure relates to methods of controlling the state of a virus (lytic or lysogenic) in an individual, such as a method of reactivating a latent virus in an individual, comprising administering an agent that modulates the activity of signal transducer and activator of transcription 3 (STAT3), p300, CBP, or p300/CBP. Optionally, the methods may further comprise a histone deacetylase (HDAC) inhibitor.

BACKGROUND

Exemplary viral pathogens for humans include Herpes simplex viruses 1 and 2 (HSV-1 and HSV-2), which are common human pathogens that are transmitted from person to person by physical contact between infected and uninfected tissues. Characteristically, these viruses vigorously replicate at the portal of entry into the body. Concurrently they are transported retrograde to neurons of ganglia innervating that site [Roizman et al., Herpes simplex viruses. in: Knipe, D. M., Howley, P. M. (Eds.), *Fields Virology*, sixth ed. 2013. Lippincott Williams & Wilkins, Philadelphia]. In neurons, the viruses establish a latent infection [Al-Dujaili et al., Future Microbiol, 6: 877-907 (2011); Roizman et al., Annu Rev Microbiol 41: 543-71 (1987)]. In the course of latent infection, the genes expressing the viral proteins are repressed [Perng et al., Interdiscip Perspect Infect Dis 2010: 262415 (2010); Knipe et al., Virology 435: 141-56 (2013)] and only a long non-coding RNA designated as latency associated transcript (LAT) [Farrell et al., Proc Natl Acad Sci USA, 88: 790-4 (1991); Spivack et al., J Virol 65: p. 6800-10 (1991); Mitchell et al., J. Gen. Virol. 71: 125-132 (1990); Held et al, J Neurovirol 17: 518-27 (2011)] and micro RNAs are expressed [Cui et al., J Virol 80: p. 5499-508 (2006); Umbach et al., Nature 454: 780-3 (2008); Munson et al., Arch Virol 157: 1677-88 (2012)]. Periodically in response to physical, hormonal, or emotional stress, the virus replicates and is transported to a site at or near the portal of entry into the body where it can cause a lesion. Virus made in the lesion can be transmitted to a non-infected individual [Perng et al., Interdiscip Perspect Infect Dis 2010: 262415 (2010)].

The fundamental problems associated with HSV infections are multifold. HSV-1 is transmitted primarily by oral contact. While in most individuals the recurrent lesions occur at the mucocutaneous region of the lip or genitals (classical fever blisters), the virus is occasionally transported to the brain where it causes encephalitis or to the eye where it causes herpes keratitis. Encephalitis typically occurs in 1 in 100,000 individuals per year, and can cause severe sequelae, including death [Steiner, Curr Opin Neurol 24: 268-74 (2011)]. Recurrent herpes keratitis is a major cause of blindness in the United States [Farooq et al., Sury Ophthalmol 57: 448-62 (2012)]. The problems associated with HSV-2 genital infections can be overwhelming, particularly if the recurrences are frequent, painful or transmitted to a newborn.

Studies on viral latency published to date indicate that: (1) Viral genes form several groups that are coordinately and sequentially derepressed upon productive infection in cell culture and also at the portal of entry into the body [Roizman et al., Cell Cycle 4: 1019-1021 (2005); Roizman et al., J Neurovirol 17: 512-7 (2011)]. Thus, α genes are derepressed with the involvement of VP16, a protein brought into cells during infection [Proenca et al., J Gen Virol 92: 2575-85 (2011)]. At least one a protein designated ICP0 plays a key role in the derepression of β and at least a large fraction of γ genes [Gu et al., Proc Natl Acad Sci USA 104: 17134-9 (2007)]. Following a single incubation of intact trigeminal ganglia in medium containing anti-nerve growth factor (NGF) antibody, genes representative of all coordinately regulated viral genes are derepressed at once in the absence of prior protein synthesis [Du et al., Proc Natl Acad Sci USA 108: 18820-4 (2011)]. In effect, the mechanism of reactivation does not involve VP16 or ICP0; and (2) one hypothesis that could explain the massive derepression of all viral genes at once is that, in the absence of NGF, the neuron undergoes apoptosis [Du et al., Proc Natl Acad Sci USA 109: 14616-21 (2012)]. Indeed, exposure of trigeminal organ cultures to pro-apoptotic drugs induced activation of viral genes in the presence NGF and EGF. However, unlike the spontaneous reactivation in the absence of NGF, the reactivation of viral genes in the presence of at least one pro-apoptotic drug required concurrent protein synthesis [Zhou et al., Proc Natl Acad Sci USA 110: E498-506 (2013)].

Much of the morbidity of HSV-1 and HSV-2 infections is due to the capacity of these viruses to establish latent infections in neurons and to reactivate. In most instances, the replication of HSV-1 and HSV-2 can be controlled by existing antiviral drugs. Importantly, however, antiviral drugs have no effect on latent virus, reactivation frequency or shedding. Adding to the pressure to eliminate reactivating virus is evidence that individuals with recurrent genital HSV infections are more susceptible to HIV infection than those that are not infected.

SUMMARY OF THE INVENTION

The disclosure generally relates to methods of controlling the state of a virus (lytic or lysogenic) in an individual, such as a method of reactivating a latent virus in an individual. According to the disclosure, the methods comprise administering an agent that modulates the activity of p300/CBP and/or signal transducer and activator of transcription 3 (STAT3). Also contemplated are methods related to each of the foregoing aspects that further comprise administering a histone deacetylase (HDAC) inhibitory agent. Thus, the disclosure is based on the discovery that administration of such an agent to modulate the activity of STAT3, p300, CBP (CREB Binding Protein, wherein CREB is cAMP Response Element Binding protein) or p300/CBP. Optionally, the methods further comprise a HDAC modulator (e.g., inhibitor or activator) that can promote or inhibit the reactivation of a latent virus in an individual. In general, (i) inhibition of STAT3 and/or (ii) activation of any of p300, CBP, or p300/CBP, wherein each of (i) and (ii) optionally further comprises a HDAC inhibitory agent, promotes reactivation of a virus in an individual. Administration of an antiviral agent allows for reduction or eradication of the reactivated virus.

Accordingly, in one aspect the present disclosure provides a method of reducing latent virus in an individual, the method comprising (i) administering an amount of one or more agents to the individual that (a) inhibits activity of signal transducer and activator of transcription 3 (STAT3), or (b) activates any of p300, CBP, or p300/CBP; wherein the one or more agents promotes reactivation of the latent virus, and (ii) administering an amount of an antiviral agent to the individual, thereby reducing latent virus in the individual. In some embodiments, the method comprises administering an agent that inhibits STAT3 and an agent that activates any of p300, CBP, or p300/CBP. In some embodiments, at least one of the one or more agents activates p300/CBP. Some of these embodiments further comprise administering a HDAC inhibitory agent.

In some embodiments, the one or more agents that inhibits activity of STAT3 is/are selected from the group consisting of cucurbitacin I, niclosamide, cryptotanshinone, SD 1008, Stat3 Inhibitor III, WP1066, Nifuroxazide, Stat3 Inhibitor, Stattic, S3I-201; Stat3 Inhibitor VIII, 5,15-DPP, 2-Hydroxy-4-(((4-methylphenyl)sulfonyloxy)acetyl)amino)-benzoic acid (NSC74859) and Kahweol. In an additional embodiment, the one or more agents that activates p300/CBP is MSG I.

In further embodiments, methods disclosed herein further comprise administering an amount of one or more HDAC inhibitory agents, wherein inhibition of the activity of the HDAC by the one or more HDAC inhibitory agents promotes reactivation of the virus. In related embodiments, the one or more HDAC inhibitory agents is selected from the group consisting of the following categories of HDAC inhibitors: a hydroxamic acid (or hydroxamate), a cyclic tetrapeptide, a depsipeptide, a benzamide, an electrophilic ketone, an aliphatic acid compound, nicotinamide, an NAD derivative, dihydrocoumarin, naphthopyranone, and a 2-hydroxynaphaldehyde. In some embodiments, the HDAC inhibitory agent is selected from the group consisting of sodium butyrate, vorinostatin (SAHA), valproic acid, trichostatin A (TSA), trapoxin B, phenylbutyrate, valproic acid, belinostat (PXD101), LAQ824, panobinostat (LBH589), entinostat (MS-275), CI994, (E)-3-(4-((E)-3-(3-fluorophenyl)-3-oxoprop-1-enyl)-1-methyl-1H-pyrrol-2-yl)-N-hydroxyacrylamide (MC1568) and mocetinostat (MGCD0103).

In a further aspect of the disclosure, a method of inhibiting reactivation of a virus in an individual is provided, the method comprising administering an amount of one or more agents to the individual that: (a) activates signal transducer and activator of transcription 3 (STAT3), or (b) inhibits any of p300, CBP or p300/CBP; wherein the one or more agents inhibits reactivation of the virus. In some embodiments, at least one of the one or more agents inhibits p300/CBP.

In some embodiments, the one or more agents that activate STAT3 is selected from the group consisting of an interferon, epidermal growth factor, interleukin-5, interleukin-6, interleukin-10, hepatocyte growth factor, leukemia inhibitory factor, bone morphogenetic protein 2 and leptin. In further embodiments, the one or more agents that inhibit p300, CBP, or p300/CBP is selected from the group consisting of delphinidin, C646, curcumin, garcinol, and anacardic acid.

In some embodiments, the methods described herein further comprise administering an amount of one or more HDAC activating agents that activates a histone deacetylase (HDAC), wherein activation of the HDAC by the one or more HDAC activating agents inhibits reactivation of the virus. In related embodiments, the one or more HDAC activating agents is ITSA1 (N-(1H-Benzotriazol-1-yl)-2,4-dichlorobenzamide).

In another embodiment, the methods described herein comprise administering an amount of one or more serine/threonine protein kinase inhibitors, wherein administering the serine/threonine protein kinase inhibitor promotes reactivation of the virus. In one embodiment, the serine/threonine protein kinase inhibitor is rapamycin and the target is mammalian target of rapamycin (MTOR, also known as FRAP1). MTOR is a phosphatidylinositol 3'-kinase-related kinase. In some embodiments, the serine/threonine protein kinase inhibitor is MK-2206 and the target is Akt.

In some embodiments, the methods described herein comprise administering an amount of one or more phosphatidylinositol 3'-kinase (PI3K) inhibitors, wherein administering the phosphatidylinositol 3'-kinase (PI3K) inhibitor promotes reactivation of the virus. In some embodiments, the phosphatidylinositol 3'-kinase (PI3K) inhibitor is GDC-0941. In some embodiments, the phosphatidylinositol 3'-kinase (PI3K) inhibitor is BEZ-235.

In any of the aspects or embodiments of the disclosure, the virus is selected from the group consisting of a herpes virus, a human cytomegalovirus, a varicella-zoster virus and a human immunodeficiency virus. In one embodiment, the herpes virus is herpes simplex virus 1 (HSV-1). In another embodiment, the herpes virus is herpes simplex virus 2 (HSV-2).

(2011)] 30 days after inoculation of mice with HSV-1(F) were processed immediately after excision (columns 1 and 5), or after 24 hour incubation in medium containing NGF+EGF (columns 2 and 6) or NGF+EGF+CTB (200 µM, 500 µM, columns 3 and 7, 4 and 8, respectively). Normalized copies of viral mRNAs (ICP27, TK, VP16, UL41, LAT), mirH3, mirH5, and mirH6 are shown.

Figure 3:
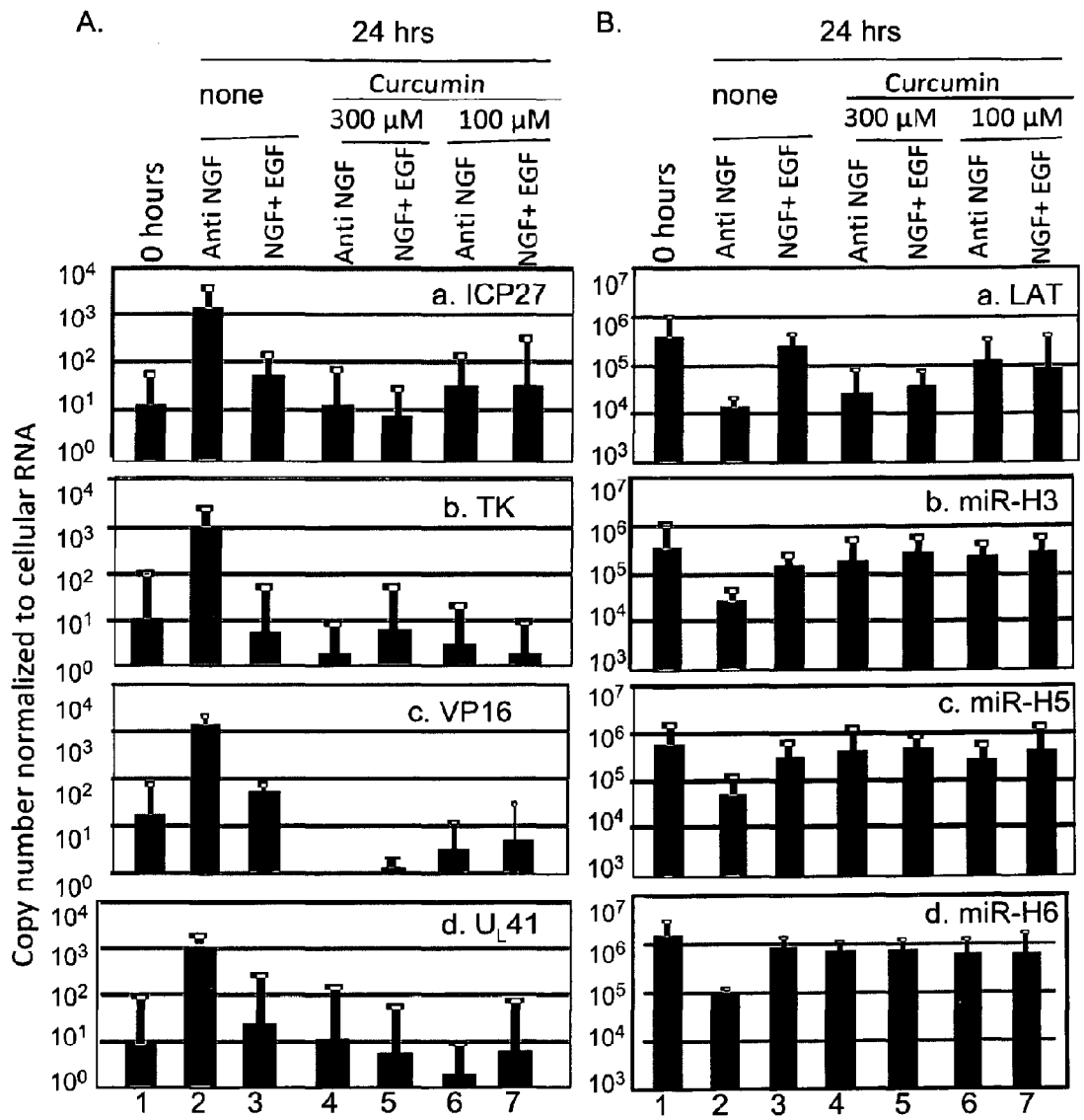

FIG. 3 depicts viral genes, LAT, and miRNA expression during virus reactivation from latently infected ganglia treated by a P300 inhibitor (Curcumin). TG excised 30 days after inoculation of HSV-1(F) were processed immediately after excision (columns 1), or after 24 hour incubation in medium containing anti-NGF antibody (columns 2), anti-NGF antibody+curcumin (100 µM, 300 µM, columns 4 and 6, respectively), NGF+EGF (columns 3), or NGF+EGF+curcumin (100 µM, 300 µM, columns 5 and 7, respectively). Viral mRNAs (ICP27, TK, VP16, UL41, LAT) and viral miRNAs (mirH3, mirH5, and mirH6) were measured and normalized to cellular RNA.

Figure 4:
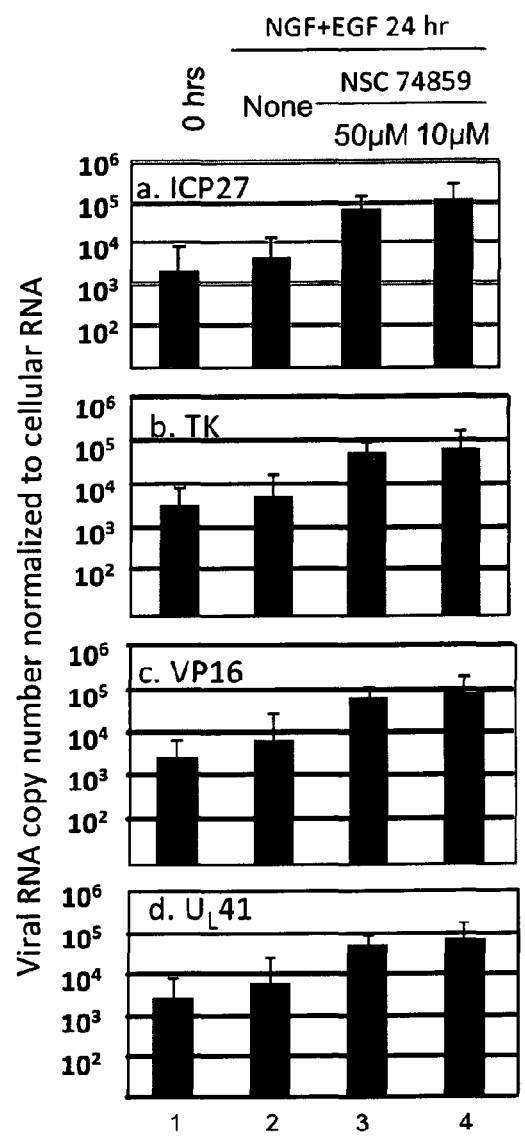

FIG. 4 shows HSV-1(F) reactivation from latency induced by STAT3 inhibitor (NSC74859). TG excised on 30 day after inoculation of HSV-1(F) were processed immediately (column 1), or after 24 hour incubation in medium containing NGF+EGF (column 2) or NGF+EGF+NSC74859 (10 mM and 50 µM, columns 3 and 4, respectively). Normalized copies of ICP27, TK, VP16 and UL41 are shown.

Figure 5:
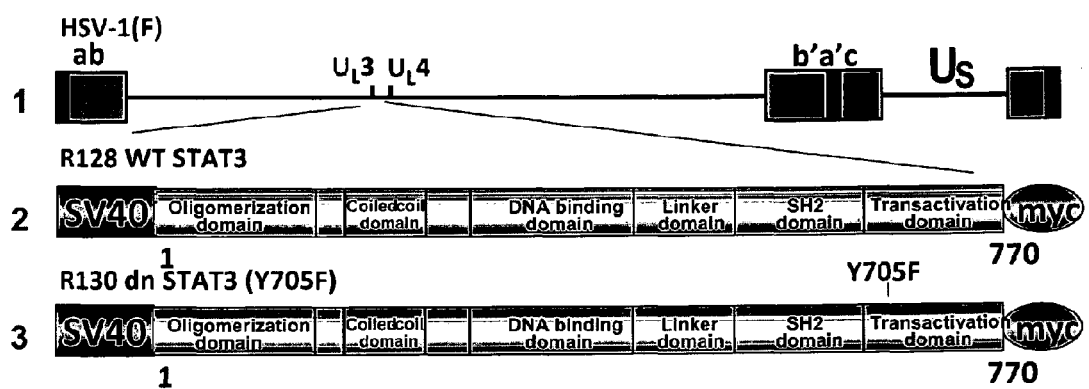

FIG. 5 shows a schematic representation of the recombinant viruses carrying wild-type or dominant-negative human STAT3 in the HSV-1(F) genome. Line 1: DNA sequence arrangement of HSV-1 DNA. Line 2: Schematic representation of HSV-1 recombinant virus expressing wild-type STAT3 designated as R128 and arrangement of STAT3 functional domains. Line 3: Schematic representation of HSV-1 recombinant virus expressing dominant negative STAT3 (with a single substitution of Y705F resulting from an A→T transversion at nucleotide 2114) designated as R130. Wide-type or dominant negative STAT3 with myc tag flanked by the SV40 promoter and poly(A) sequence were inserted between the $U_L3$ and $U_L4$ genes.

Figure 6:
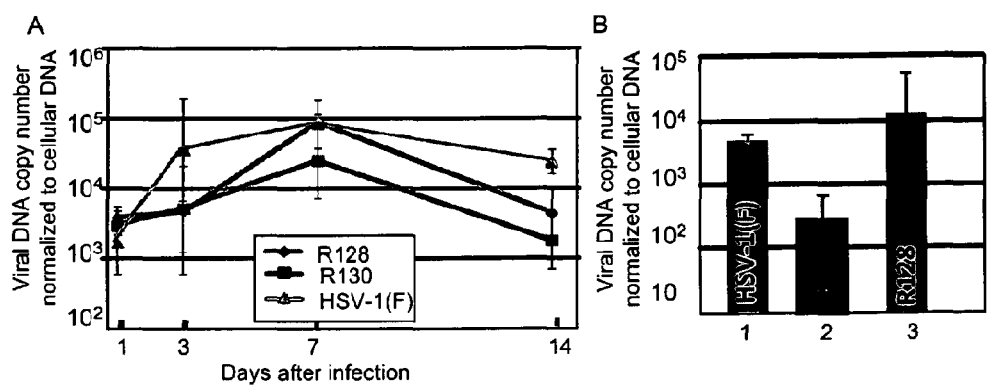

FIG. 6 shows the accumulation of viral DNA in TG of mice infected with wild-type or recombinant viruses. On indicated days after infection with HSV-1(F), R128 or R130 viruses, the TG were removed and extracted. The DNA copy numbers, normalized to 50 ng cellular DNA, are shown as a function of days after infection. Panel A: DNA copy number in murine TG at days 1-3, 7 and 14 after infection. Panel B: DNA copy number in TG 30 days after infection.

Figure 7:
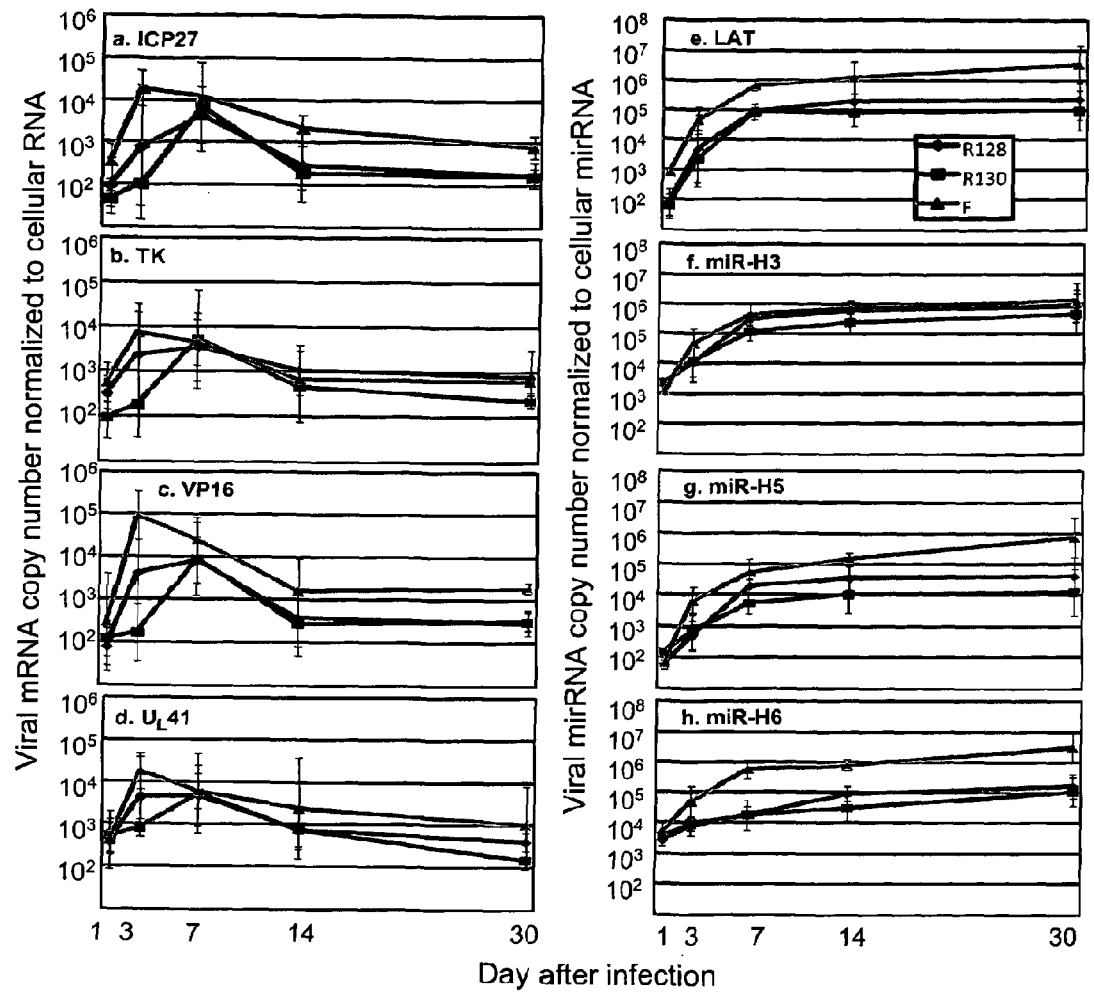

FIG. 7 depicts gene expression in murine TG after infection with R128 or R130 recombinant viruses. On indicated days after infection with HSV-1(F), R128 or R130 viruses, mouse TG were removed, extracted and subject to RNA assay. The relative number of copies of mRNAs encoding ICP27 (a), TK (b), VP16 (c), UL41 (d), or the LAT (e) normalized to cellular RNA, and mirH3 (f), mirH5 (g), mirH6 (h) normalized with respect to cellular miRNA, are shown as a function of days after infection.

Figure 8:
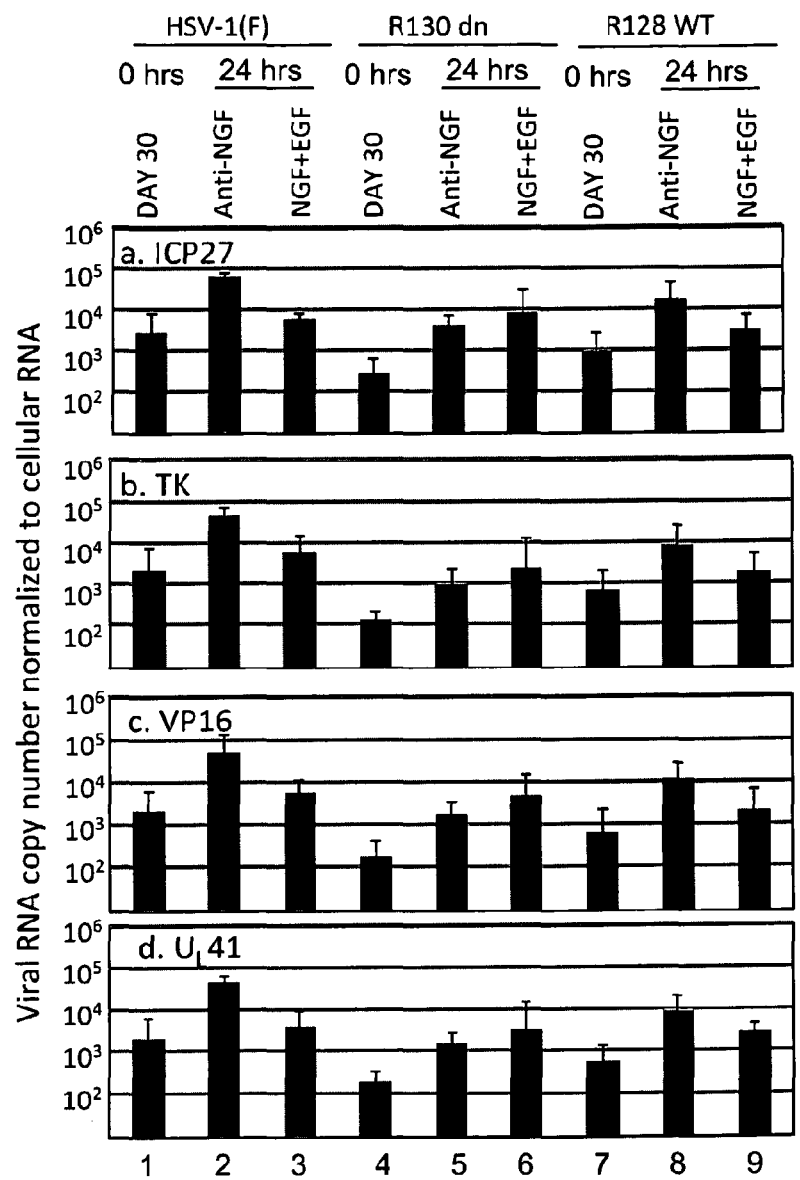

FIG. 8 shows the reactivation of latent HSV-1(F), R128 and R130 viruses in TG at 24 hours after excision and incubation in medium containing anti-NGF antibody or NGF+EGF. At 30 days post-inoculation, TG excised from the wild-type or recombinant viruses were processed immediately (Columns 1, 4, 7) or after 24 hour incubation in medium containing anti-NGF antibody (Columns 2, 5, 8) or NGF+EGF (Columns 3, 6, 9). Copy numbers of mRNAs encoding ICP27 (a), TK (b), VP16 (c), UL41 (d), normalized to cellular RNA, are shown.

Figure 9:
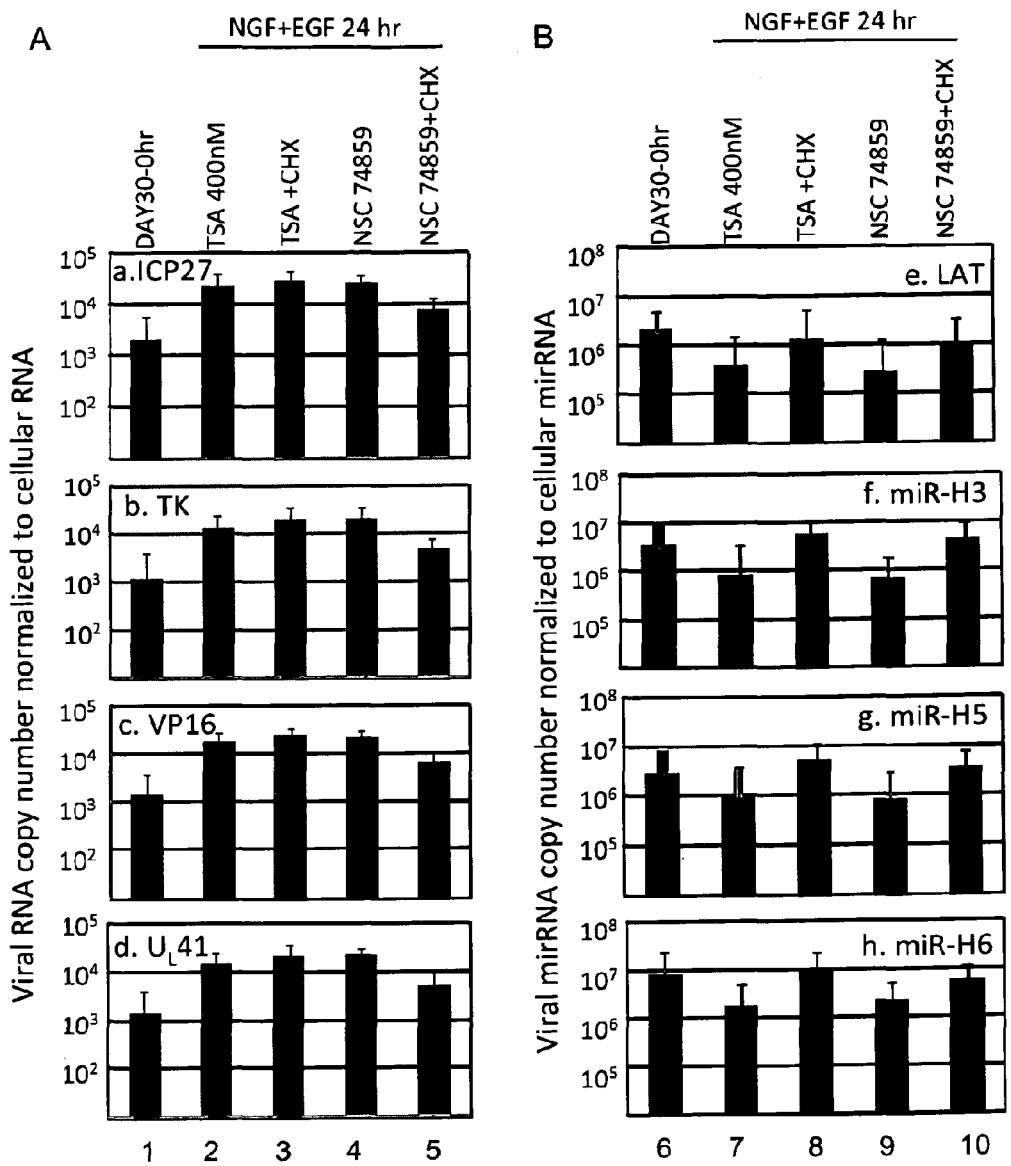

FIG. 9 shows the reactivation of latent HSV-1(F) in murine ganglia incubated in medium containing the HDAC inhibitor TSA or the STAT3 inhibitor NSC74859 in the presence or absence of cycloheximide. TG excised on day 30 after infection with HSV-1(F) were processed immediately (columns 1 and 6), or after 24 hours of incubation in medium containing NGF+EGF+TSA (400 nM) (columns 2 and 7), NGF+EGF+TSA+cycloheximide (CHX, 150 µg/ml, columns 3 and 8), NGF+EGF+NSC74859 (10 µM, columns 4 and 9) or NGF+EGF+NSC74859+CHX (columns 5 and 10). Normalized copies of viral mRNAs (ICP27, TK, VP16, UL41) the LAT, mirH3, mirH5, and mirH6 are shown.

Figure 10:
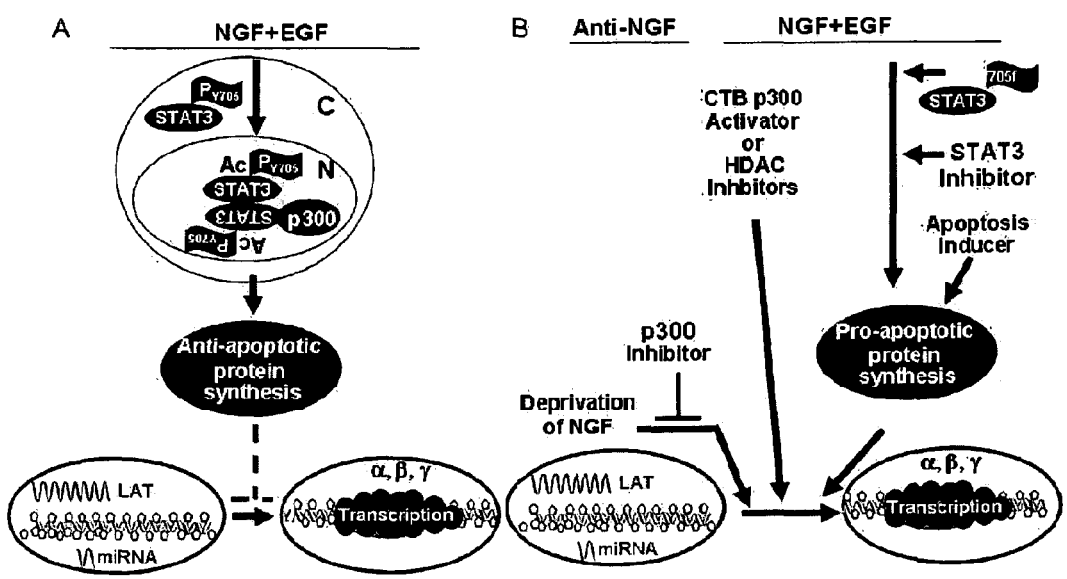
Figure 11A:
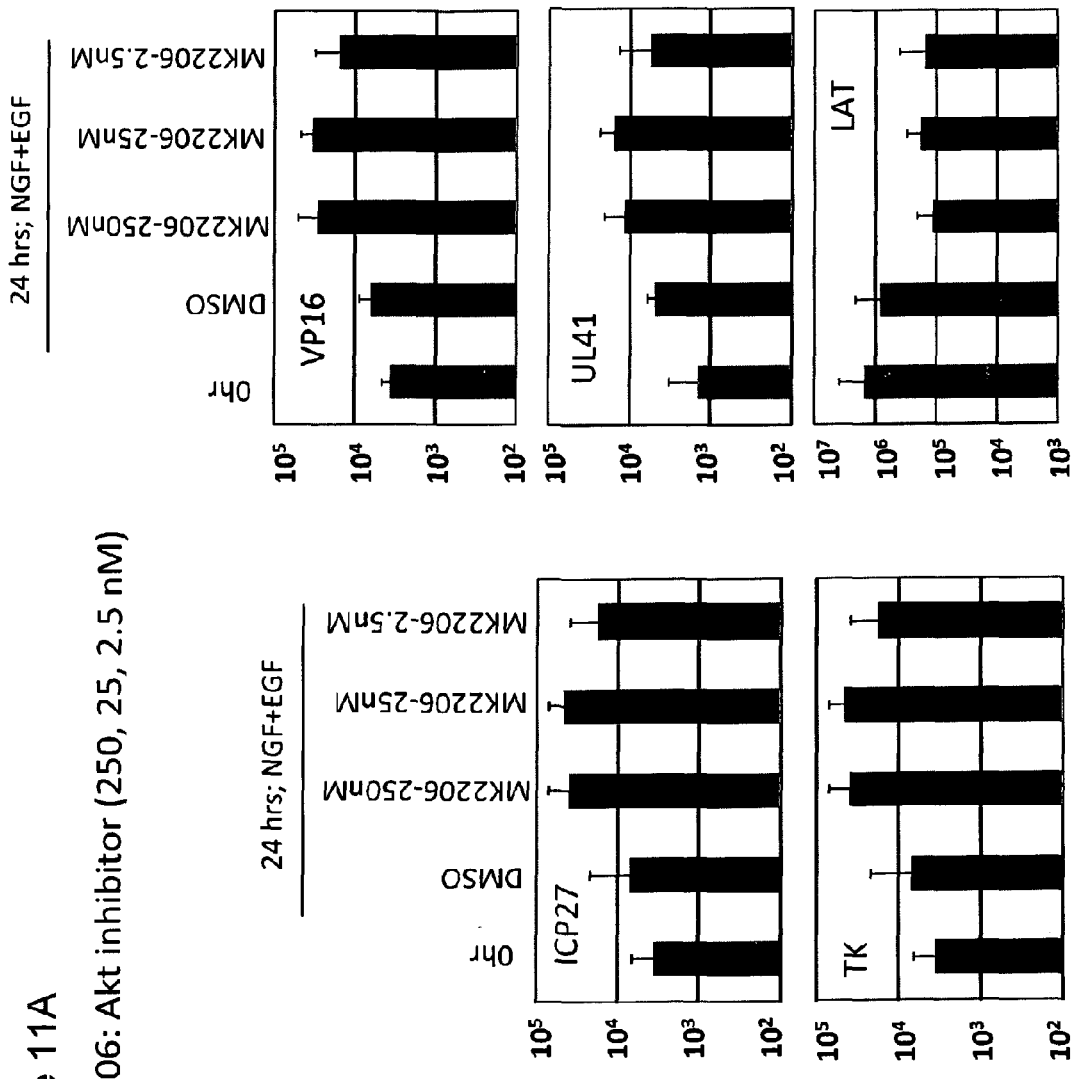
Figure 11B:
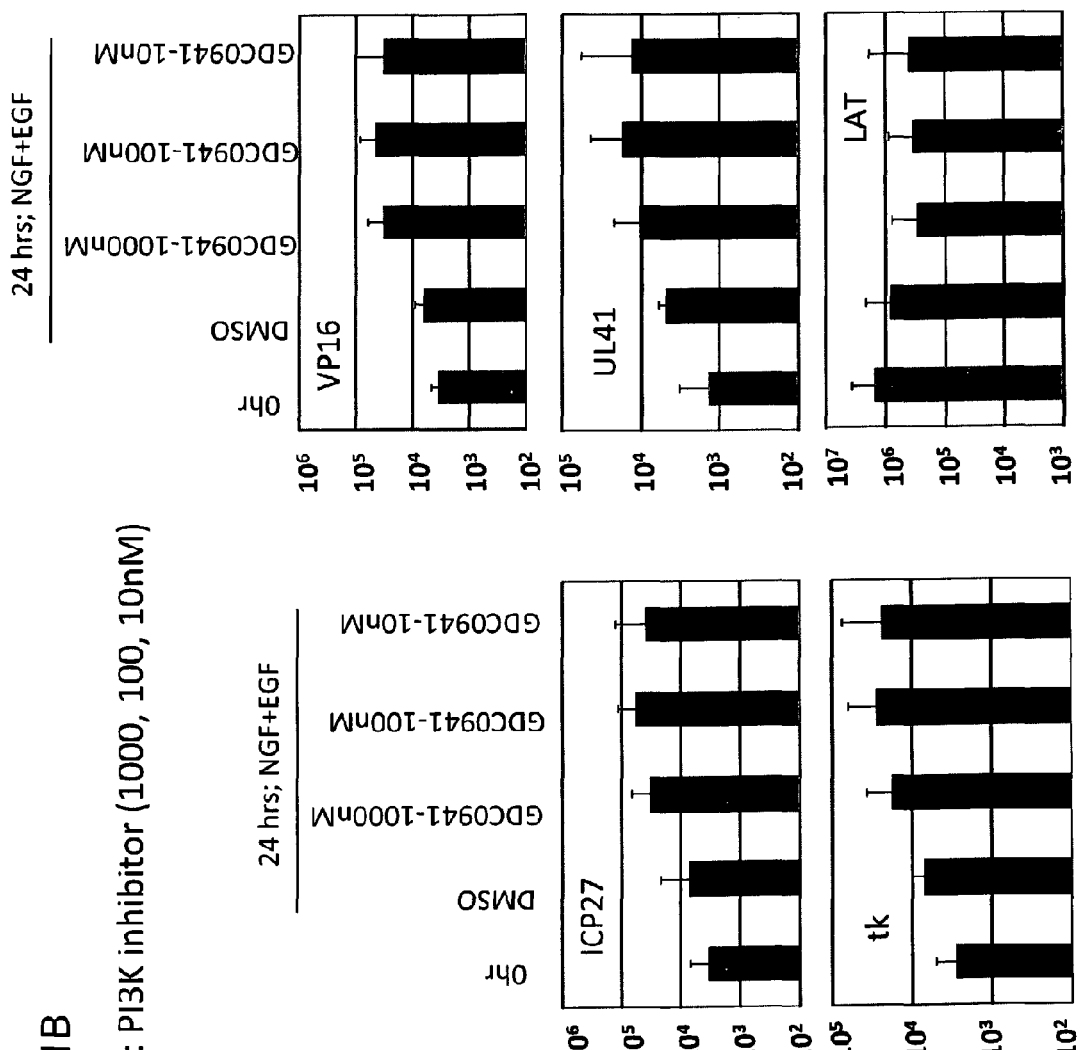
Figure 11C:
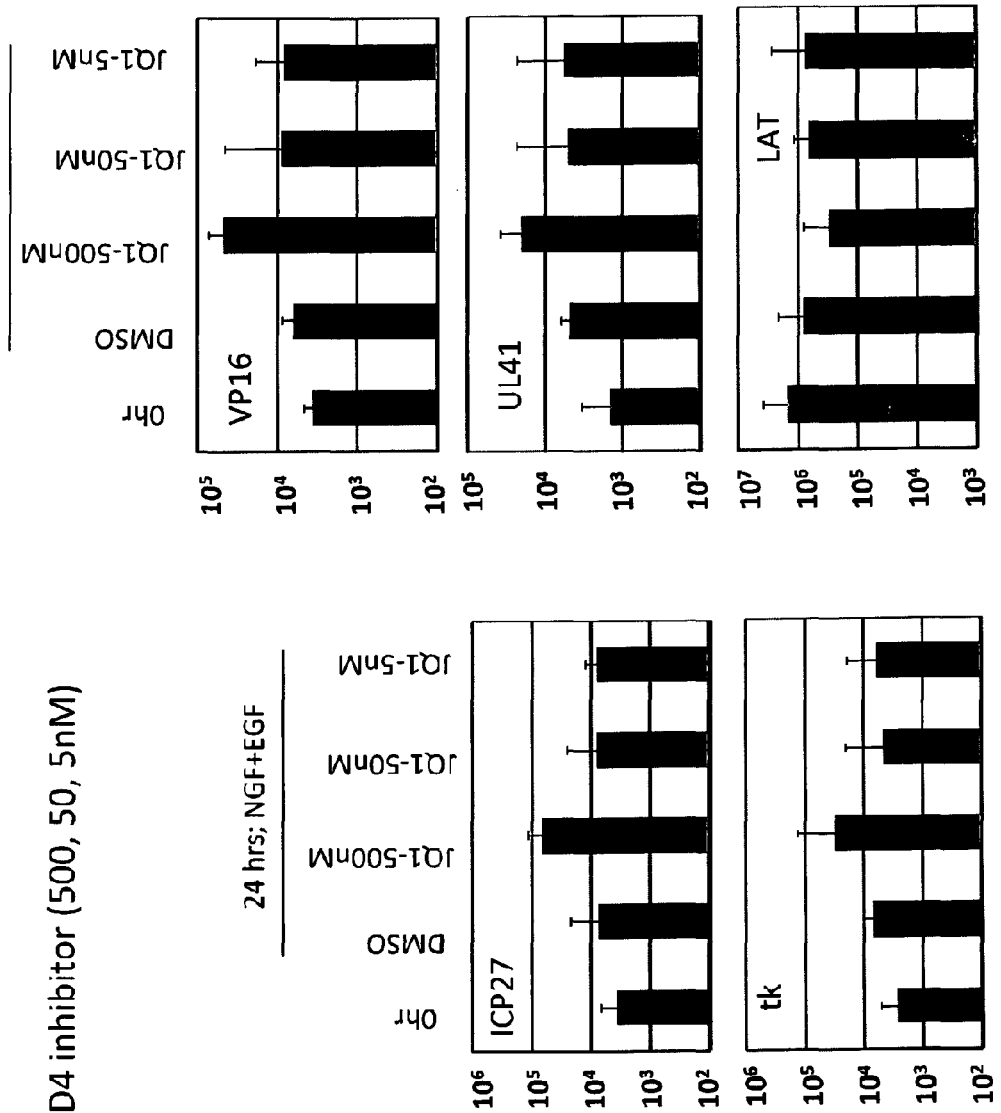
Figure 11D:
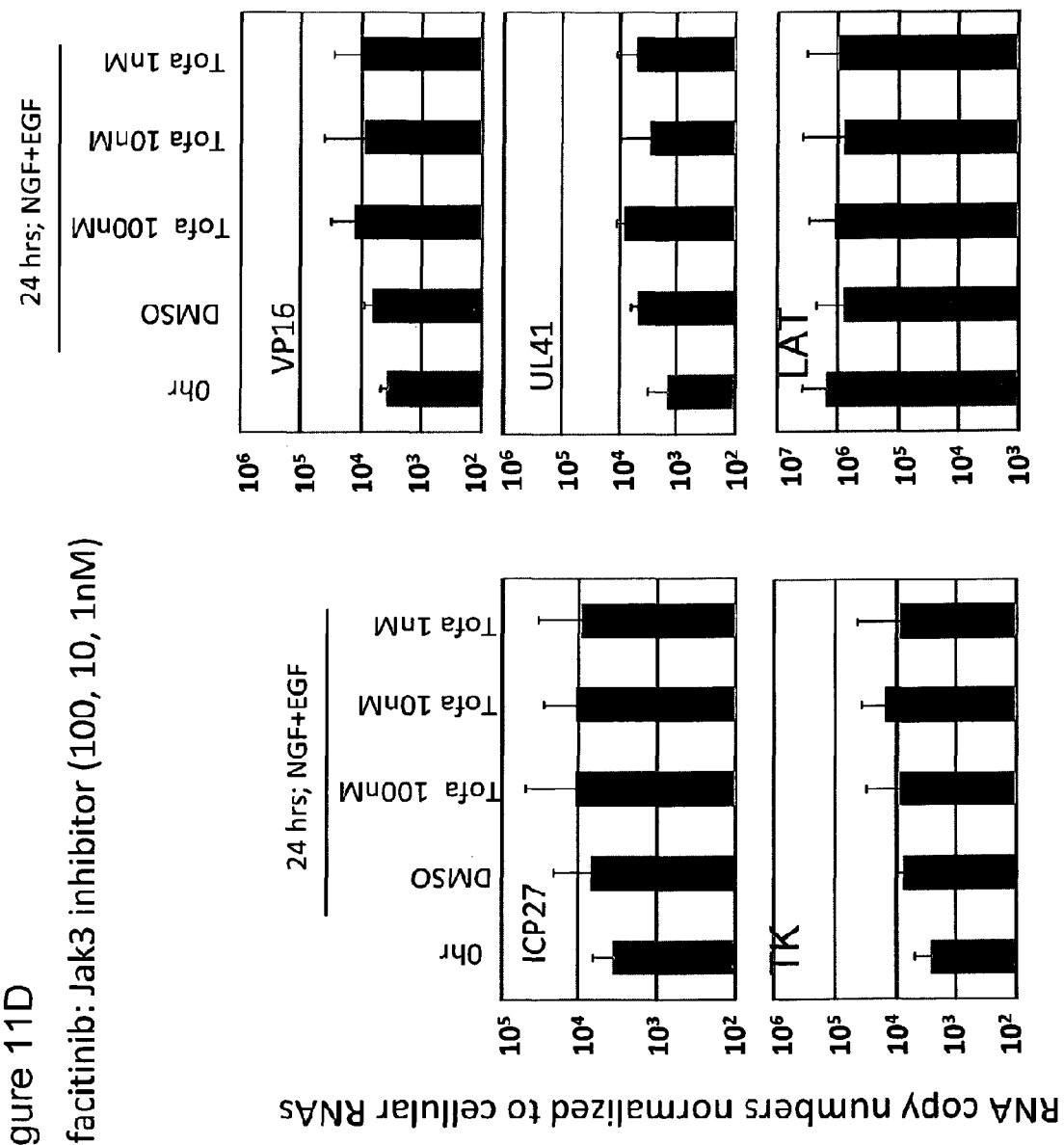
Figure 11E:
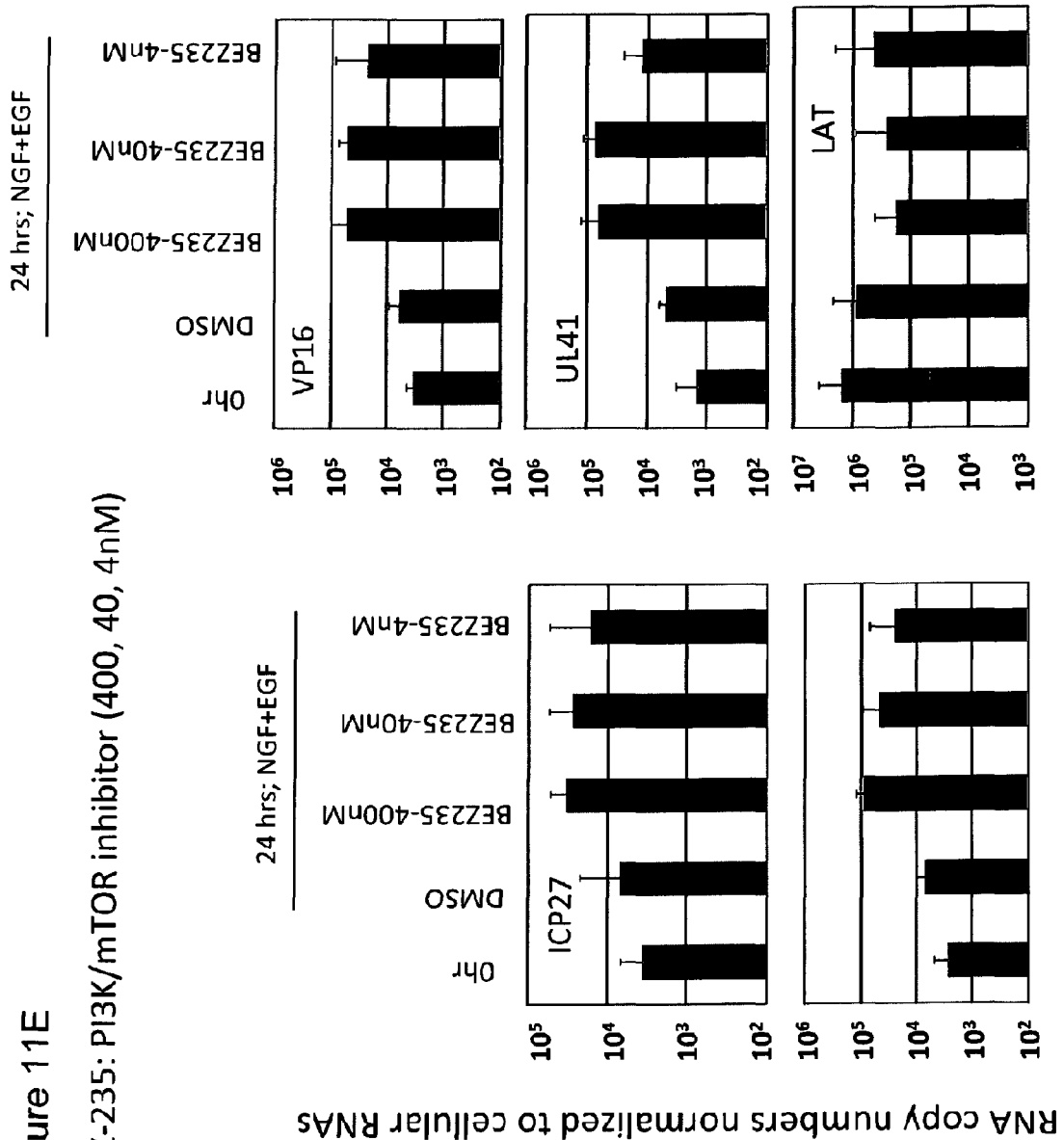
Figure 11F:
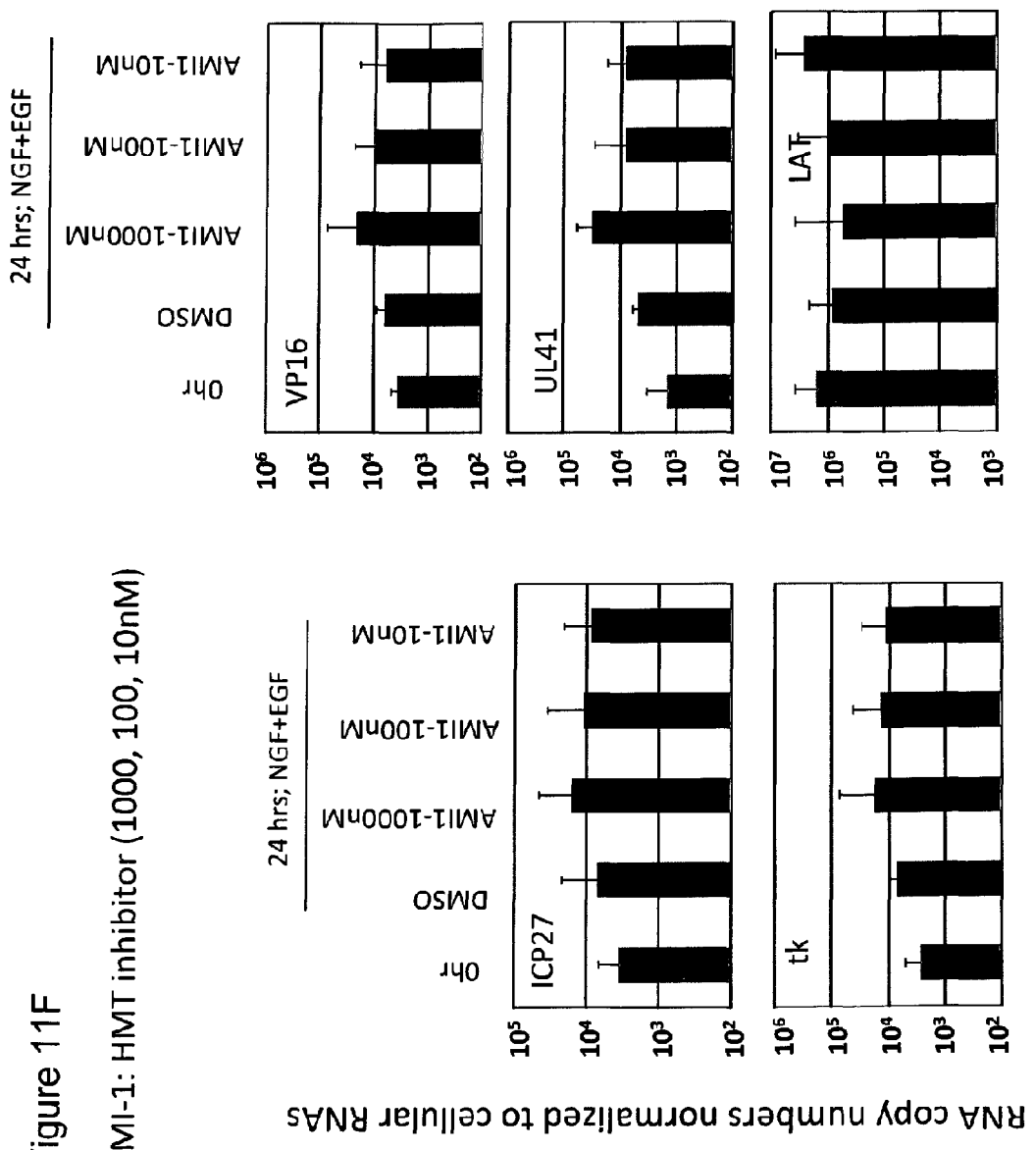
Figure 11G:
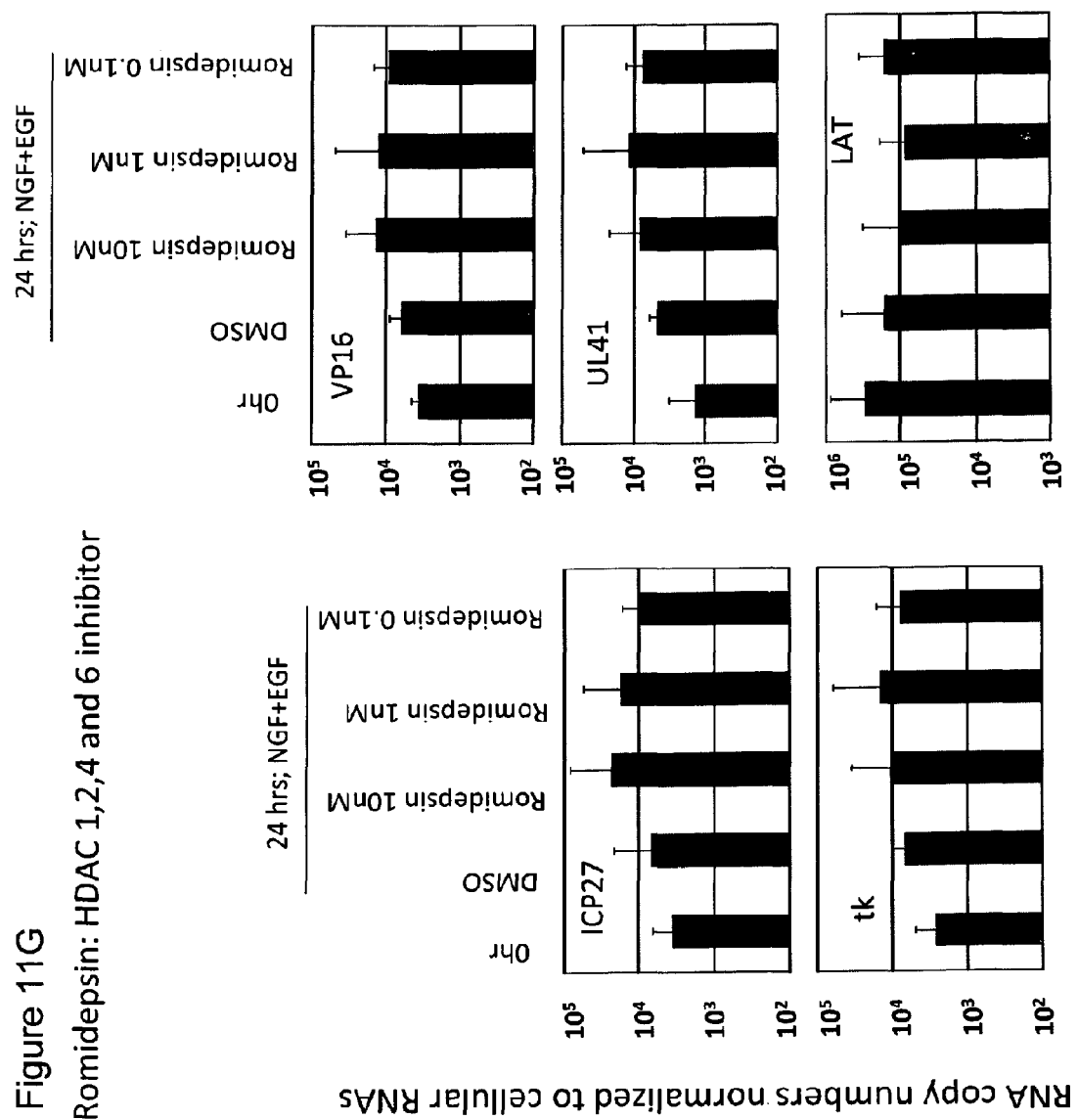
Figure 11H:
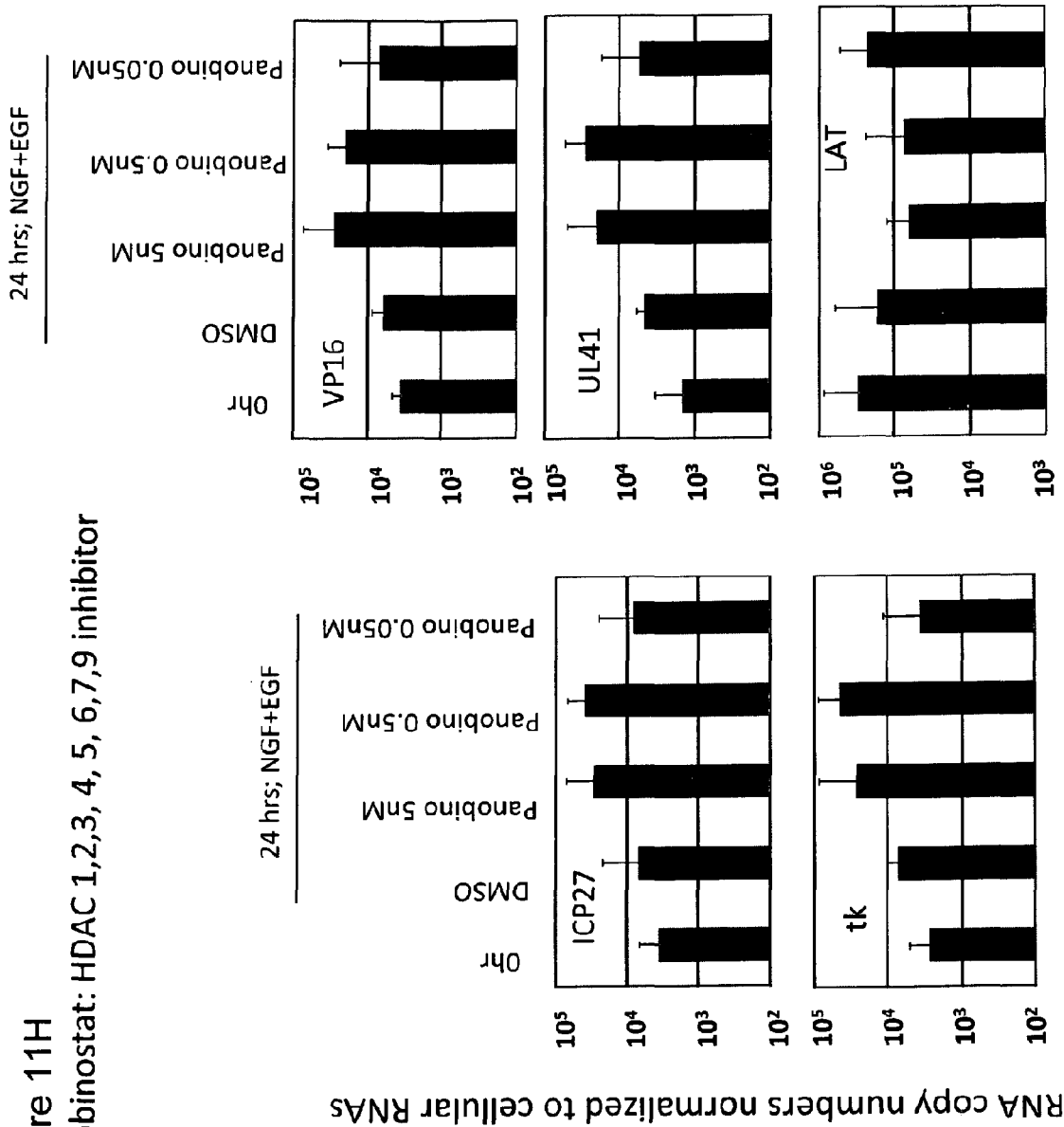
Figure 11I:
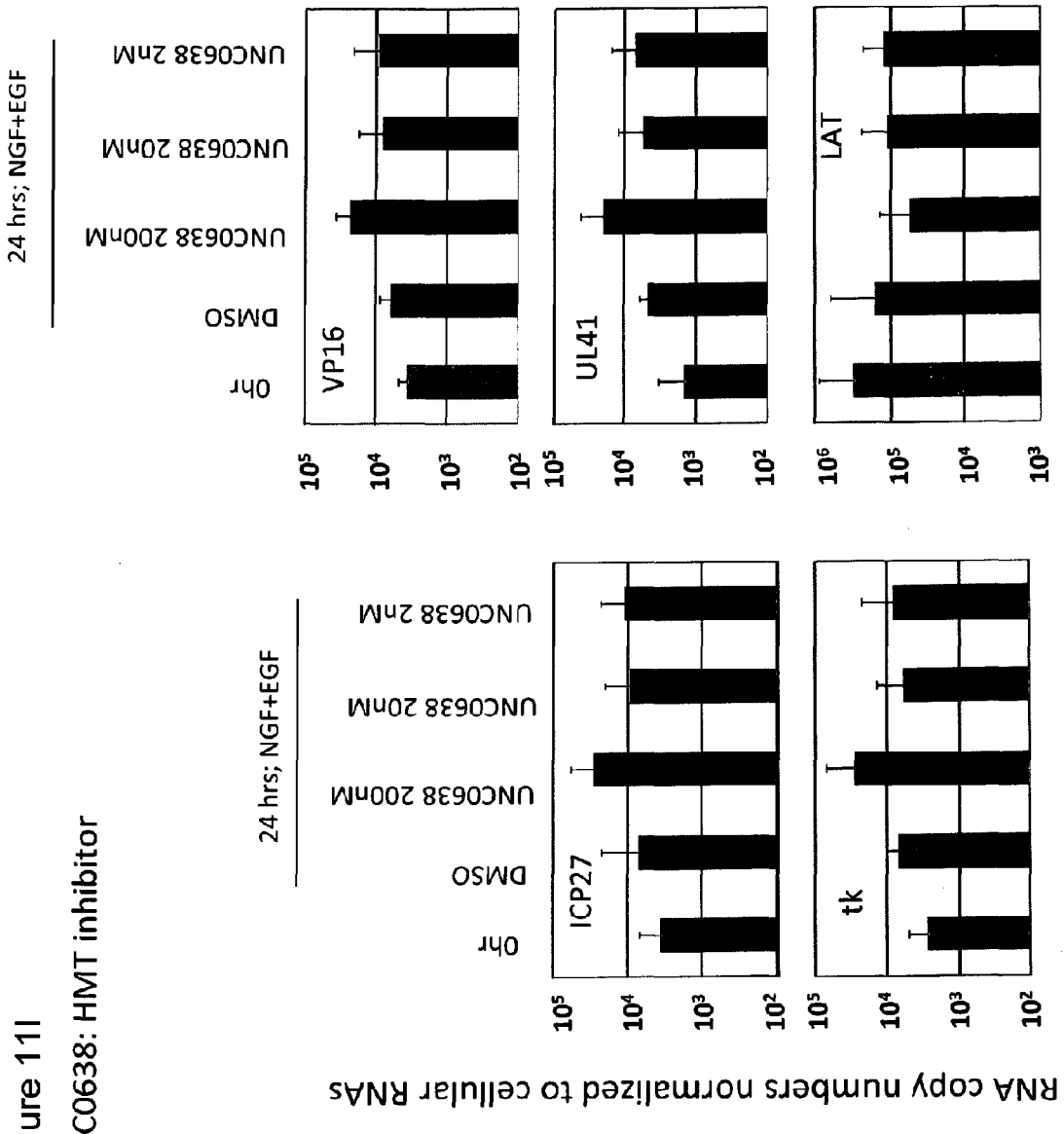
Figure 11J:
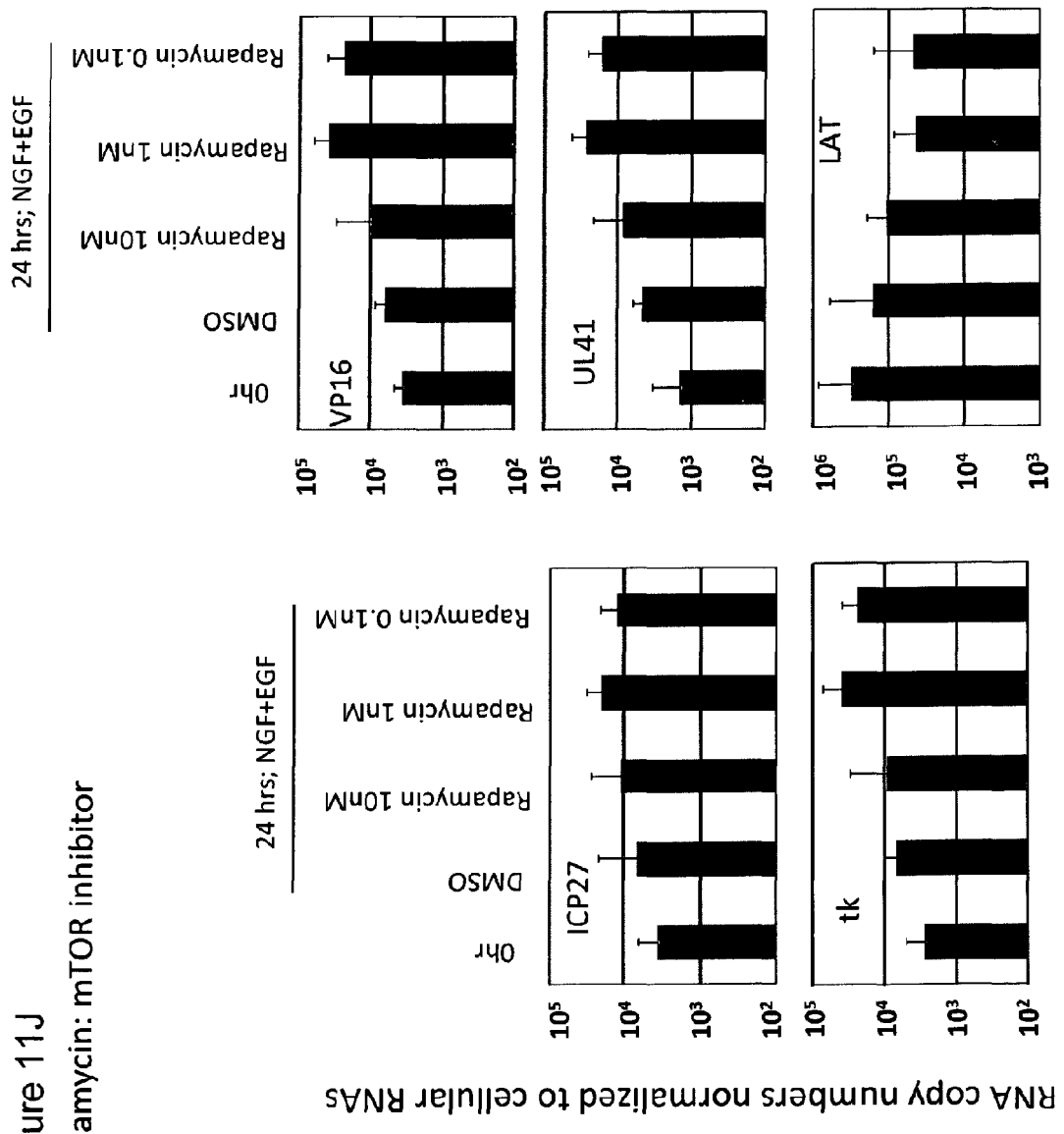

FIG. 10 depicts a schematic representation of the roles of STAT3, HDAC, and p300/CBP in the transcriptional activation of latent HSV-1 as a function of STAT3, HDAC and p300/CBP. Panel A. STAT3 activated by stress or cytokines is translocated to the nucleus where it forms dimers, recruits p300/CBP and induces the expression of genes involved in neuronal protection, neuronal degeneration or development. The results shown schematically in Panel A indicate that activated STAT3 blocks reactivation of latent virus in ganglia maintained in the presence of NGF and EGF. Panel B. Reactivation of latent virus is induced by maintaining ganglia in medium deprived of NGF in the absence of de novo protein synthesis. Reactivation in the absence of de novo protein synthesis is induced by inhibition of HDAC or by activation of p300/CBP. Reactivation is also induced by inhibitors of STAT3, by a dominant negative STAT3, or by pro-apoptotic drugs, but in these instances reactivation requires de novo protein synthesis.

FIG. 11 depicts the raw data for the results listed in Table 1 (see Example 1, below). The experimental design utilized was similar to that reported in Du et al., [Proc. Natl. Acad. Sci. (USA) 110(28): E2621-E2628 (2013), incorporated herein by reference]. Each bar represents an average of six ganglia. Compounds tested and depicted are (A) MK-2206 (Akt inhibitor); (B) GDC0941 (PI3K inhibitor); (C) JQ1 (BRD4 inhibitor); (D) Tofacitinib (Jak3 inhibitor); (E) BEZ-235 (PI3K/mTOR inhibitor; (F) AMI-1 (HMT inhibitor); (G) Romidepsin (HDAC 1, 2, 4, and 6 inhibitor; (H) Panobinostat (HDAC 1, 2, 3, 4, 5, 6, 7, and 9 inhibitor); (I) UNC0638 (HMT inhibitor); (J) Rapamycin (mTOR inhibitor).

DETAILED DESCRIPTION OF THE INVENTION

Integration of viral genomes into a host chromosome is mandatory for the successful completion of the life cycle of several viruses, including retroviruses and adeno-associated-viruses (AAV). In contrast, Herpesviruses maintain their genomes as extra-chromosomal circular episomes in the nuclei of infected cells without the need for integration. However, several reports of chromosomally integrated herpesvirus (CI-HHV) DNA have appeared over the years suggesting that Herpesviruses can indeed integrate into the host chromosomes under certain circumstances. In addition, for a virus such as the human herpesvirus 6 (HHV-6), found integrated in the germ line of approximately 1% of the world's population, integration may represent more than sporadic or anecdotal events [Morissette et al., J. Virol. 84(23): 12100-9 (2010)].

Herpesviruses are members of a diverse family of viruses that colonize all vertebrates from fish to mammal. Although more than one hundred herpesviruses exist, all are architecturally nearly identical, with a genome consisting of a linear double-stranded DNA molecule (100-225 kilobase pairs)

protected by an icosahedral capsid made up of 162 hollow center capsomeres, a tegument surrounding the nucleocapsid and a viral envelope derived from host membranes. Upon infection, the linear viral DNA is delivered to the nucleus where it circularizes to form the viral episome. Depending on several factors, the viral cycle can either proceed to a productive infection or to a state of latency. In either case, the viral genetic information is maintained as extra-chromosomal circular DNA. Interestingly however, certain oncogenic Herpesviruses such as Marek's disease virus and Epstein-Barr virus can be found integrated at low frequencies in a host chromosome. These events were mostly viewed as anecdotal findings and considered exceptions rather than properties of Herpesviruses [Morissette et al., J. Virol. 84(23): 12100-9 (2010)].

A key property of herpes simplex viruses (HSV), therefore, is their ability to establish latent infection in sensory or autonomic ganglia and to reactivate on physical, hormonal or emotional stress. In latently infected ganglia, HSV expresses a long non-coding RNA and a set of micro RNAs, but viral proteins are not expressed. The mechanism by which latent HSV reactivates is unknown. A key question is the mechanism of reactivation in the absence of tegument proteins that enable gene expression in productive infections. It has been reported that the use of ganglionic organ cultures enables rapid reactivation in medium containing antibody to never growth factor (NGF) or delayed reactivation in medium containing NGF and epidermal growth factor (EGF). It has also been reported that in ganglionic organ cultures incubated in medium containing antibody to NGF, all viral genes are derepressed at once without requiring de novo protein synthesis within the timeframe of a single replicative cycle.

Upon infection of an individual by a virus, an individual is often administered an antiviral agent in order to combat the infection. If a virus has the ability to establish latency within the individual, however, then eradication of the active virus in the individual via the administration of the antiviral agent does not rid the individual of the virus. A virus that can establish latency possesses the ability to reactivate on physical, hormonal or emotional stress. Thus, the individual typically harbors the virus for the duration of their lifespan. Without wishing to be bound by theory, it is contemplated by the present disclosure that by stimulating the reactivation of a latent virus in an individual, the reactivated virus is then susceptible to an antiviral agent acting at any point in the lytic life cycle. For example, reactivation of the virus could result in lysis of the cell harboring the virus and expulsion of mature virus particles that would be susceptible to an antiviral agent resulting in viral destruction. Further, lysis of the cell that harbored the latent virus also results in the cells' destruction. In such a way, optionally including multiple rounds of latent virus reactivation and administration of an antiviral agent, the viral load in an individual is reduced or the virus is eradicated from an individual.

It is noted here that, as used in this specification and the appended claims, the singular forms "a," "an," and "the" include plural reference unless the context clearly dictates otherwise.

As used herein, the term "inhibits" as relates to the inhibition of a protein such as STAT3, p300, CBP, p300/CBP or HDAC, means to lower the activity of the protein. By way of example, it is understood that an agent of the disclosure that inhibits STAT3 activity reduces its activity relative to its activity in the absence of the agent. The disclosure contemplates any degree of inhibition of the activity of the protein by the agent, including an inhibition of 5%, 10%, 20%, 30%, 40%, 50%, 60%, 70%, 80%, 90% 95%, 99% or 100% relative to the activity of the protein in the absence of the agent. The activity of a protein can be determined in vitro by one of ordinary skill in the art using any of a number of conventional methodologies.

Similarly, the term "activates" as relates to the activation of a protein such as STAT3, p300, CBP, p300/CBP or HDAC, means to increase the activity of the protein. In some embodiments, activation of p300/CBP promotes its histone acetyltransferase activity. By way of example, it is understood that an agent of the disclosure that increases the activity STAT3 increases its activity relative to its activity in the absence of the agent. The disclosure contemplates any degree of increase of the activity of the protein by the agent, including an increase of 1%, 2%, 5%, 10%, 20%, 30%, 40%, 50%, 60%, 70%, 80%, 90%, 95%, 99% or 100% relative to the activity of the protein in the absence of the agent. The activity of a protein can be determined in vitro by one of ordinary skill in the art.

The term "an amount," as used herein, refer to an amount of a compound sufficient to treat, ameliorate, or prevent the identified disease or condition, or to exhibit a detectable therapeutic, prophylactic, activating or inhibitory effect. The effect can be detected by, for example, an improvement in clinical condition, or a reduction in symptoms. The precise amount for a subject will depend upon the subject's body weight, size, and health; the nature and extent of the condition; and the therapeutic or combination of therapeutics selected for administration. Where a drug has been approved by the U.S. Food and Drug Administration (FDA), "an amount" refers to a dosage approved by the FDA or its counterpart foreign agency for treatment of the identified disease or condition.

As used herein, "concomitant use" is understood to be interchangeable with concurrent administration or co-administration. Thus, the terms are understood to encompass administration simultaneously, or at different times, and by the same route or by different routes, as long as the two agents are given in a manner that allows both agents to be affecting the body at the same time. For example, concomitant use can refer to a medication concomitantly administered, whether prescribed by the same or a different practitioner, or for the same or a different indication.

Agent

The term "agent" as used herein refers to a substance or a derivative thereof that acts to reduce or increase the activity of a protein relative to the activity of the protein in the absence of the agent. In various aspects, the agent is one that activates or inhibits a protein selected from the group consisting of STAT3, p300, CBP and p300/CBP. Thus, in some embodiments, the disclosure contemplates that p300 or CBP is inhibited or is activated independently of the other. Further, in some embodiments, a HDAC modulatory agent, such as a HDAC inhibitory agent or a HDAC activating agent, is administered.

In some aspects, the disclosure provides methods of reducing latent virus in an individual, the method comprising administering an amount of one or more agents to the individual that inhibits activity of signal transducer and activator of transcription 3 (STAT3). In various embodiments, the inhibitor of STAT3 is selected from the group consisting of cucurbitacin I, niclosamide, cryptotanshinone, SD 1008, Stat3 Inhibitor III, WP1066, Nifuroxazide, Stat3 Inhibitor, Stattic, Stat3 Inhibitor, S3I-201; Stat3 Inhibitor VIII, 5,15-DPP, 2-Hydroxy-4-(((4-methylphenyl)sulfonyloxy)acetyl)amino)-benzoic acid (NSC74859) and Kahweol.

In further aspects of the disclosure, methods are provided to reduce latent virus in an individual, the method comprising administering an amount of one or more agents to the individual that (a) inhibits activity of STAT3 or (b) activates any of p300, CBP or p300/CBP, wherein the one or more agents promotes reactivation of the latent virus. In some embodiments, a plurality of agents is administered, with at least one agent inhibiting STAT3 activity and at least one other agent activating any of p300, CBP or p300/CPB. In one embodiment, the activator of p300/CBP is MSG I.

In additional aspects, the disclosure provides methods of reducing latent virus in an individual, the method further comprising administering an amount of one or more HDAC inhibitory agents, wherein inhibition of the activity of the HDAC by the one or more HDAC inhibitory agents promotes reactivation of the virus. HDAC inhibitory agents are well known in the art and, in various embodiments, the one or more HDAC inhibitory agents is selected from the group consisting of the following categories of HDAC inhibitors: hydroxamic acids (or hydroxamates), cyclic tetrapeptides, depsipeptides, benzamides, electrophilic ketones, aliphatic acid compounds, nicotinamide, NAD derivatives, dihydrocoumarin, naphthopyranone, and 2-hydroxynaphaldehydes. In some embodiments, the HDAC inhibitor is selected from the group consisting of sodium butyrate, vorinostatin (SAHA), valproic acid, trichostatin A (TSA), trapoxin B, phenylbutyrate, valproic acid, belinostat (PXD101), LAQ824, panobinostat (LBH589), entinostat (MS-275), CI994, (E)-3-(4-((E)-3-(3-fluorophenyl)-3-oxoprop-1-enyl)-1-methyl-1H-pyrrol-2-yl)-N-hydroxyacrylamide (MC1568) and mocetinostat (MGCD0103).

In some aspects, a method of inhibiting reactivation of a virus in an individual is provided, the method comprising administering an amount of one or more agents to the individual that: (a) activates signal transducer and activator of transcription 3 (STAT3), or (b) inhibits any of p300, CBP, or p300/CBP; wherein the one or more agents inhibits reactivation of the virus.

In some embodiments, the one or more agents that activate STAT3 is selected from the group consisting of an interferon, epidermal growth factor, interleukin-5, interleukin-6, interleukin-10, hepatocyte growth factor, leukemia inhibitory factor, bone morphogenetic protein 2 and leptin.

In some embodiments, the one or more agents that inhibit any of p300, CBP, or p300/CBP is selected from the group consisting of delphinidin, C646, curcumin, garcinol, and anacardic acid.

In still further embodiments, the disclosure provides methods of inhibiting reactivation of a latent virus in an individual, the method further comprising administering an amount of one or more HDAC activating agents, wherein activation of the HDAC by the one or more agents inhibits reactivation of the virus. In various embodiments, the one or more HDAC activating agents is ITSA1 (N-(1H-Benzotriazol-1-yl)-2,4-dichlorobenzamide).

Adjunct/Combination Therapy

The disclosure contemplates that, in any of the methods described herein, one or more additional agents are co-administered with an agent as described herein. The additional therapeutic, for example, is an anti-viral agent. The additional therapeutic can be administered prior to, concurrent with, or after administration of an agent and/or a HDAC modulating agent according to the disclosure.

The term "anti-viral agent" as used herein for adjunct therapy refers to substances that act to maintain, reduce or eliminate the amount of virus present in the mammal being treated herein. Antiviral agents that can be used in combination with an agent of the disclosure include, but are not limited to, non-nucleoside reverse transcriptase inhibitors, nucleoside reverse transcriptase inhibitors, protease inhibitors, and fusion inhibitors. In various embodiments, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide. The disclosure further contemplates embodiments comprising combinations of anti-viral agents as disclosed herein.

Additional, non-limiting examples of antiviral agents contemplated for use in combination with an agent of the disclosure (i.e., a modulator, such as an inhibitor or activator, of STAT3, p300 and/or CBP) and/or in combination with an HDAC modulating agent include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of antiviral agents include, but are not limited to, acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

Viruses

The disclosure provides, in various aspects, methods of reducing the amount of latent virus in an individual comprising the steps of administering an agent of the disclosure and an antiviral agent. The disclosure also provides methods of inhibiting the reactivation of a latent virus in an individual by administering an agent of the disclosure and/or an HDAC modulating agent. Agents of the disclosure and/or HDAC modulating agents useful in at least one of these methods will be apparent from the disclosure of the particular agent or HDAC modulating agent provided herein.

The methods of the disclosure are applicable to any virus that has the ability to establish latency in an individual, such as a human individual. By way of non-limiting example, viruses contemplated by the disclosure include a herpes virus, a human cytomegalovirus, a varicella-zoster virus and a human immunodeficiency virus (HIV). In some embodiments, the herpes virus is herpes simplex virus 1(HSV-1) or herpes simplex virus 2 (HSV-2). In further embodiments, the individual is infected with more than one virus. For example and without limitation, the individual may be infected with HSV-1 and HSV-2, or the individual may be infected with HSV-1 and HIV, or the individual may be infected with HSV-2 and HIV.

Humans can be infected by eight different types of herpes virus. Herpes simplex viruses I and II and varicella zoster virus are alphaherpesviruses. Cytomegalovirus and the roseoloviruses, human herpesviruses 6 and 7, are classified as betaherpesviruses. Epstein-Barr virus and Kaposi's sarcoma-associated herpesvirus belong to the gammaherpesvirus subfamily [Muylaert et al., J. Biol. Chem. 286(18): 15619-15624 (2011)]. The present disclosure contemplates that the methods described herein are applicable to any one or more of the herpesviruses.

The disclosure will be more fully understood by reference to the following examples which detail exemplary embodiments of the disclosure. The examples should not, however, be construed as limiting the scope of the disclosure. All citations throughout the disclosure are hereby expressly incorporated by reference.

EXAMPLES

The experiments described below were designed to define the role played by specific regulatory pathways in the maintenance of viral genes in a repressed state in trigeminal ganglia harboring HSV-1 in a latent, silent state. The general experimental design was as follows: Mice were inoculated by the corneal route with wild-type or mutant viruses. Wild-type HSV-1 replicates in the eye, is transported retrograde to trigeminal ganglia and replicates in some neurons, but is silenced and is retained in a latent state in other neurons [Du et al., Proc Natl Acad Sci USA 107: 15904-9 (2010)]. By day 30 after infection, the ganglia contained only silenced, latent virus. The objective was to analyze the events that take place within a 24 hour interval after induction of reactivation, which is within the timeframe of a single virus replicative cycle. To achieve this objective, ganglia were excised and incubated intact in medium containing antibody to nerve growth factor (NGF) or in medium containing both NGF and epidermal growth factor (EGF). Deprivation of NGF leads to activation of viral gene expression and abrogation of latency [Zhou et al., Proc Natl Acad Sci USA 110: E498-506 (2013)]. In the presence of both NGF and EGF, reactivation is delayed [Du et al., Proc Natl Acad Sci USA 108: 18820-4 (2011)].

The following experiments detail the role of STAT3 and p300/CBP in reactivation of HSV-1 in latently infected ganglia. In the first series of experiments, inhibition of histone deacetylating enzymes and activation of histone acetyl transferase p300/CBP is shown, resulting in reactivation of latent virus, whereas inhibition of p300/CBP suppresses reactivation. In the second series of experiments it is shown that STAT3 plays a key role in the maintenance of HSV-1 in a latent form inasmuch as interference with its activity induces reactivation.

Specifically, the examples demonstrate that latent HSV in ganglia immersed in medium containing NGF and EGF is reactivated by (a) broad spectrum HDAC as well as specific histone deacetylase-1 (HDAC1) or histone deacetylase-4 (HDAC4) inhibitors (b) activation of p300/CBP and (c) either STAT3 carrying the Y705F amino acid substitution or an inhibitor of STAT3. Conversely, reactivation of latent HSV was blocked by p300/CBP inhibitor in medium containing antibody to NGF. The results establish a role for STAT3 in the maintenance of the latent viral state and interference with its activity leads to reactivation. Further, the disclosure herein establishes a role for p300, CBP and p300/CBP in viral reactivation.

Example 1

HDAC Inhibitors Activate Latent Virus in the Ganglionic Organ Culture Model

Figure 1:
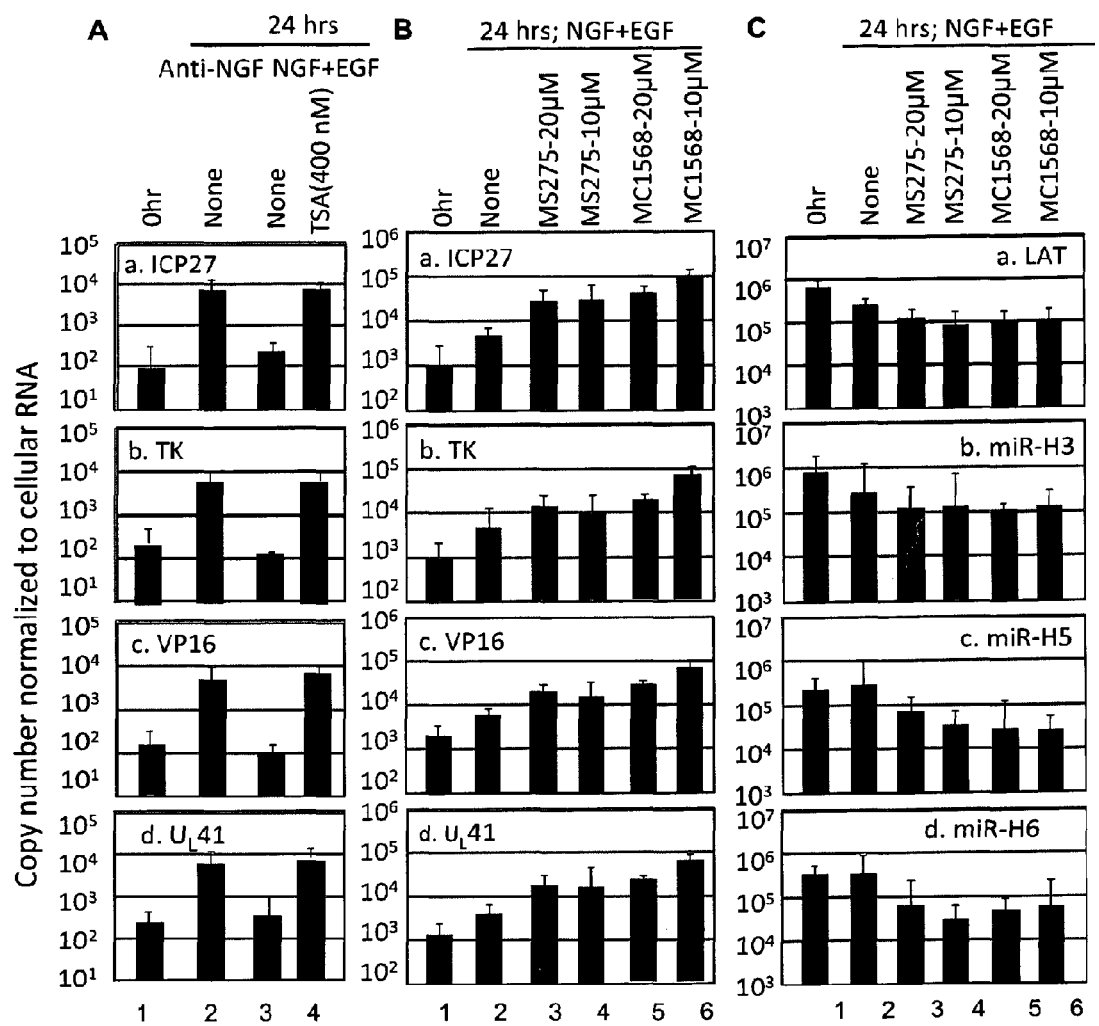
FIG. 1 shows the effect of HDAC inhibitors (TSA, MS275, MC1568) on HSV-1(F) reactivation. Murine TG (trigeminal ganglia) excised 30 days after infection with HSV-1(F) by the corneal route were processed immediately after excision, or after 24 hour incubation in medium containing anti-NGF antibody, NGF+EGF, NGF+EGF+TSA (400 nM) (Panel A), NGF+EGF+MS275 (10 µM, 20 µM, Panel B and C), or NGF+EGF+MC1568 (10 µM, 20 µM, Panel B and C). The figure shows the geometric mean amounts of viral mRNAs normalized to 50 ng cellular RNA or viral miRNAs normalized to $10^8$ copies of cellular miRNA quantified by Let-7a (host cell miRNA standard). In the foregoing, the concentrations of NGF and EGF were 1 µg/ml each; the concentrations of the drug (MS275 or MC1568) was as indicated. The numbers shown hereafter are geometric means±standard errors based on assays of 6 TG/group.

Earlier studies have shown that HSV-1 can be reactivated from latently infected neurons by HDAC inhibitors [Robert et al., J Neurovirol. 11: 306-317 (2006)]. These studies verified that HDAC inhibitors, both broad spectrum and those with some degree of specificity, reactivated HSV-1 in latently infected trigeminal ganglia maintained in organ culture incubated in medium containing NGF+EGF. In this series of experiments three inhibitors were tested. Trichostatin A (TSA) is a broad spectrum HDAC inhibitor [Robert et al., J Neurovirol. 11: 306-317 (2006); Kazantsev et al., Nat Rev Drug Discov 7: 854-68 (2008)]. Earlier studies showed that it induces the reactivation of latent virus in neurons harboring latent virus [Robert et al., J Neurovirol. 11: 306-317 (2006)]. MS275 and MC1568 at low concentrations act as specific inhibitors of HDAC 1 and 4, respectively [Nebbioso et al., EMBO Rep 10: 776-82 (2009); Khan et al., Biochem J 409: 581-9 (2008)]. At high concentrations their specificity decreases. All three induced the reactivation of HSV in trigeminal ganglia harvested 30 days after infection and incubated in medium containing NGF and EGF (FIG. 1 Panels A and B). As in earlier studies, the results show the geometric mean levels of viral mRNAs from six ganglia extracted at the time of excision and at 24 hours after excision. As previously reported, LAT and miRNAs decrease in amounts (Panel C) concurrent with accumulation of viral gene products (Panel B).

Figure 2:
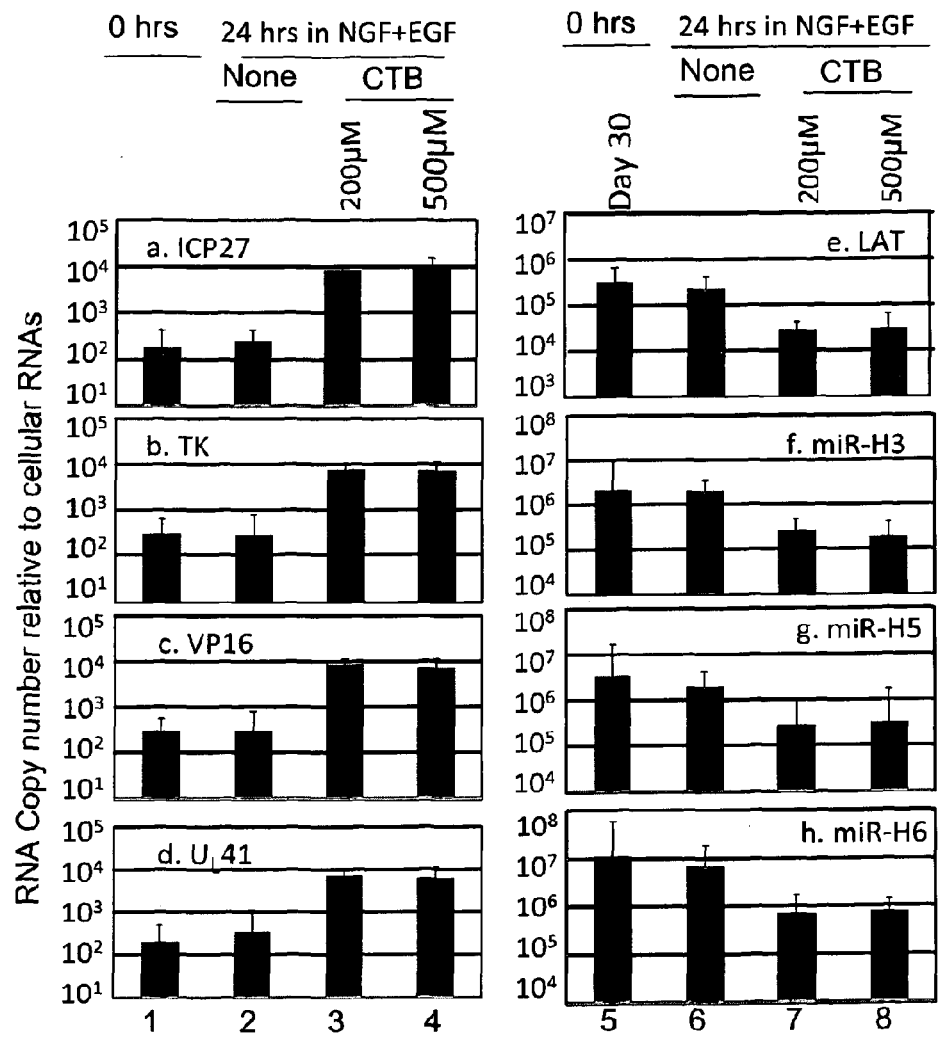
FIG. 2 depicts HSV-1(F) reactivation from latency induced by the p300/CBP activator CTB. Surgically excised TG [Du et al., Proc Natl Acad Sci USA 108: 18820-18824

Activation of p300/CBP Induces Reactivation of Latent Virus. Conversely, Inhibition of p300/CBP Blocks Reactivation Two series of experiments were conducted. In the first, ganglia excised from mice inoculated at least 30 days earlier were incubated in medium containing NGF+EGF and supplemented with N-(4-Chloro-3-trifluoromethyl-phenyl)-2-ethoxy-benzamide (CTB). CTB is a powerful activator of the histone acetyltransferase activity of P300/CBP by binding and altering the structure of the enzyme [Balasubramanyam et al., J Biol Chem 278: 19134-40 (2003)]. At 24 hours after incubation, the ganglia were extracted and analyzed for the presence of mRNA representative of the four groups of viral mRNAs and also for the presence of the LAT and viral miRNAs. As shown in FIG. 2, following exposure to the drug all viral mRNAs increased approximately 50-fold whereas miRNAs and the LAT decreased approximately 10-fold.

Earlier studies also showed that the spice curcumin is a potent inhibitor of the acetyl transferase activity of p300 [Balasubramanyam et al., J Biol Chem 279: p. 51163-71 (2004)]. To test whether curcumin will block reactivation, the experiment as described above was repeated but with curcumin in place of CTB. In this experiment the ganglia were incubated either in medium containing NGF+EGF or in medium containing antibody to NGF. As shown in FIG. 3, Panel A, curcumin blocked the reactivation of HSV and degradation of the LAT and miRNAs independent of the medium in which the ganglia were incubated. It is noteworthy that, in ganglia incubated in medium containing antibody to NGF, curcumin suppressed the accumulation of small amounts of mRNAs normally detected at the time of excision of the ganglia. Compare, for example, the amounts of mRNA detected in freshly excised ganglia (FIG. 3, Panel A, column 1, 0 hours) with those detected in ganglia incubated in medium containing curcumin (Panel A, columns 4 and 5). It is also noteworthy that at the higher concentration (300 μM) curcumin suppressed the accumulation of the LAT (Panel B, columns 4 and 5).

Inhibition of STAT3 Phosphorylation Induces Activation of Latent HSV

In this series of experiments we tested the effects of the STAT3 inhibitor NSC74859 on reactivation of HSV from murine trigeminal ganglia harboring latent virus [Siddiquee et al., Proc Natl Acad Sci USA 104: 7391-6 (2007)]. The experimental design was similar to that reported above. The excised ganglia were incubated in medium containing NGF+EGF and one of two concentrations of the drug. The results of analyses of the mRNAs extracted from ganglia 24 hours after excision are shown in FIG. 4. In brief, the results show that representatives of all four temporally regulated groups of viral genes were upregulated by 24 hours after excision of the ganglia and incubation in the presence of the STAT3 inhibitor. The results indicate that STAT3 plays a role in the maintenance of HSV-1 in the latent state in murine trigeminal ganglia.

Further experiments were conducted to test the effects of additional compounds for activation of latent HSV. The experimental design utilized was similar to that reported in Du et al., [Proc. Natl. Acad. Sci. (USA) 110(28): E2621-E2628 (2013), incorporated herein by reference]. In brief, thirty days after infection of the cornea the mice were euthanized. The ganglia were removed and either immediately analyzed or incubated in medium containing NGF and EGF growth factors to maintain the virus in a latent state. The drugs shown in Table 1 were added to the medium in the concentration shown to induce reactivation. Controls included incubation in medium containing antibody to NGF to induce total reactivation or NGF+EGF to maintain the virus in latent state. Twenty-four hours after excision, the ganglia were extracted and analyzed individually for four different mRNAs, Latency Associated Transcript (LAT), and three different microRNAs. Results of the experiments are shown in Table 1, below, and the raw data is depicted in FIG. 11.

TABLE 1

Compounds tested for activation of latent HSV in ganglionic organ cultures maintained in medium containing NGF and EGF.

| Compound Series | Class/Target | Concentrations Tested (nM) | Significant Activation of Latent HSV | Comments |
| --- | --- | --- | --- | --- |
| Romidepsin[1] | HDAC 1, 2, 4 and 6 | 10, 1, 0.1 | No | No activation |
| Panobinostat[2] | HDAC 1, 2, 3, 4, 5, 6, 7, 9 | 5, 0.5, 0.05 | Yes | 0.5 nM lowest effective concentration |
| UNC0638 | HMT (G9a, GLP) | 200, 20, 2 | No | Low level activation at 200 nM likely due to cellular toxicity |
| AMI-1 | Arginine HMT (PRMT) | 1,000, 100, 10 | No | No activation |
| Rapamycin[3] | mTOR | 10, 1, 0.1 | Yes | 1 nM lowest effective concentration |
| MK-2206[4] | Akt 1, 2, 3 | 250, 25, 2.5 | Yes | 2.5 nM lowest effective concentration |
| GDC-0941[5] | PI3K | 1,000, 100, 10 | Yes | 10 nM lowest effective concentration |
| BEZ-235[6] | PI3Ka-d/mTOR | 400, 40, 4 | Yes | 40 nM lowest effective concentration |
| JQ1[7] | BRD4 | 500, 50, 5 | No | Low level activation at 500 nM likely due to cellular toxicity |
| Tofacitinib[8] | Jak3 | 100, 10, 1 | No | Low level activation at 100 nM likely due to cellular toxicity |

[1]Approved for treatment of T cell lymphoma;
[2]Novartis in clinical trials for myeloma;
[3]Blocks rejection of organs in transplant patients;
[4]In clinical trials with relapse ovarian cancer;
[5]In clinical trials with metastatic breast cancer;
[6]In clinical trials for solid tumors;
[7]In clinical development as a non-hormone male contraceptive drug;
[8]Approved for treatment of moderate to severe rheumatoid arthritis.

The data shown in Table 1 support two key conclusions. First, HDACs and the PI3K-MTOR-AKT STAT3 pathway can be targeted in humans through the use of therapeutic drugs. Second, not all inhibitors targeting the same pathway are effective in reactivating virus.

Example 2

The Construction and Testing of Recombinant HSV-1 Expressing a Wild-Type and Dominant-Negative STAT3

This series of experiments verified that disruption of STAT3 function induces reactivation of latent virus, which was revealed by using viruses that deliver a wild-type or a dominant-negative STAT3(dnSTAT3) to the infected neurons.

The procedures for construction of the recombinant viruses are as follows.

Virus Strains and Cells

Vero cells originally obtained from the American Type Culture Collection were grown in Dulbecco's modified Eagle's medium supplemented with 5% fetal bovine serum. The BAC encoding the HSV-1(F) DNA was reported elsewhere [Zhou et al., Proc Natl Acad Sci USA 110: E498-506 (2013)].

Plasmid Construction STAT3, dnSTAT3

The plasmid (pMXs-STAT3) containing wild-type STAT3 is described in Takahashi et al., Cell 126: 663-76 (2006). The mutant STAT3 with a single substitution of Y705F (dnSTAT3) was obtained by usage of the QuikChange XL Site-Directed Mutagenesis Kit (Stratagene, Calif.) using two oligonucleotide primers: 5'-ggtagtgctgccccgtTcctgaagaccaagttc-3' (SEQ ID NO: 1) and 5'-gaacttggtcttcaggAacggggcagcactacc-3' (SEQ ID NO: 2).

Construction of STAT3 and dnSTAT3 Recombinant Viruses

The recombinant viruses, the gene encoding wild-type human STAT3 or dnSTAT3 were inserted between the genes encoding UL3 and UL4 under control of the SV40 promoter. The strategy of virus construction has been reported previously [Du et al., Proc Natl Acad Sci USA 107: 15904-9 (2010); Zhou et al., Proc Natl Acad Sci USA 110: p. E498-506 (2013)].

FIG. 3 shows the schematic diagrams of the domains of STAT3 and the structure of the genomes of the recombinant viruses. Specifically, the wild-type STAT3 coding sequences flanked by the SV40 early promoter at it 5' terminus and the myc tag at its 3' terminus was inserted between the UL3 and UL4 open reading frames in recombinant R128 (FIG. 5 lane 2). In R130 (FIG. 5 lane 3), an identical construct was inserted at the same location except that the tyrosine 705 was replaced by phenylalanine. The objective of the Y705F substitution was to block the phosphorylation of tyrosine705.

Murine Model of Virus Infection

Four-week-old inbred female CBA/J mice (Jackson Labs, Maine, USA) received unrestricted access to food and water. All animal studies were done according to protocols approved by the Institutional Animal Care and Use Committee. Following light scarification of the cornea, $1\times10^5$ pfu of virus were applied in a dropwise manner in a volume of 5 µl to each cornea of the mice. TG (trigeminal ganglia) were excised on indicated days and subjected to DNA replication and viral gene expressions assays.

Murine Model of Virus Reactivation and Drug Treatment

TG were removed 30 days after infection and incubated at 37° C., plus 5% $CO_2$ in medium 199V supplemented with 1 µg/ml of anti-NGF antibody (Abcam) for 24 hours. To temporarily block virus reactivation, TG were incubated in medium containing 300 ng/ml NGF+EGF (Invitrogen). TG were treated by drugs as described herein. Histone deacetylase (HDAC) inhibitor Trichostatin A (TSA), P300 inhibitor curcumin, and P300 activator N-(4-Chloro-3-trifluoromethyl-phenyl)-2-ethoxy-benzamide (CTB) were purchased from Sigma (MO, USA). HDAC class I-specific inhibitor pyridin-3-ylmethyl 4-((2-aminophenyl) carbamoyl)benzylcarbamate (MS-275) and HDACs class II specific inhibitor (E)-3-(4-((E)-3-(3-fluorophenyl)-3-oxoprop-1-enyl)-1-methyl-1H-pyrrol-2-yl)-N-hydroxyacrylamide (MC1568) were purchased from Selleck Chemicals (TX, USA). STAT3 inhibitor 2-Hydroxy-4-(((4-methylphenyl)sulfonyloxy) acetyl)amino)-benzoic acid (NSC74859) was purchased from EMD Millipore (MA, USA).

Characterization of the Courses of R128 and R130 Recombinant Virus Infections in Mice In this series of experiments the accumulation of viral DNA, mRNAs representative of the major kinetic classes of viral mRNAs, the LAT and the representative miRNAs in mice following intra corneal inoculation of mice were characterized. As in all studies reported herein, each experimental point represents the results obtained from six ganglia.

DNA Copy Number Assays

Total DNA were extracted from murine TG as reported previously [Du et al., Proc Natl Acad Sci USA, 107: 15904-9 (2010)]. The quantification of viral DNA copy numbers in TG were performed by SYBR green real-time PCR technology (StepOnePlus system, ABI) using viral Thymidine Kinase (TK) gene primers 5'-CTTAACAGCGTCAACA-GCGTGCCG-3' (SEQ ID NO: 3) and 5'-CCAAAGAGGT-GCGGGAG TTT-3' (SEQ ID NO: 4) and murine Adipsin gene primers 5'-AGTGTGCGGGGATGC AGT-3' (SEQ ID NO: 5) and 5'-ACGCGAGAGCCCCACGTA-3' (SEQ ID NO: 6) as internal control.

RNA Isolation and Assays

Depleted RNAs enriched for small RNAs (<200 nucleotides) were extracted using the mirVana miRNA isolation kit (Ambion, USA) according to the manufacturer's instructions. RNA was transcribed as described previously [Zhou et al., Proc Natl Acad Sci USA 110: E498-506 (2013)]. Viral gene RNAs and miRNAs (mir-H3, mir-H5, mir-H6) were quantified by Taqman qRT-PCR assays. Sequences of primers and probes were reported elsewhere [Zhou et al., Proc Natl Acad Sci USA 110: E498-506 (2013), incorporated herein by reference].

The salient features of the results were as follows:

FIG. 6 Panel A shows the accumulation of viral DNAs in trigeminal ganglia harvested 1, 3, 7 and 14 days after infection with wild-type HSV-1(F) recombinant viruses. Consistent with earlier studies, HSV DNA reached peak levels on day 7 and declined thereafter. In this experiment, the amounts of viral DNA accumulating in ganglia of mice infected with R130 were consistently lower than those of mice infected with wild-type virus or recombinant virus carrying wild-type STAT3.

FIG. 7 shows the patterns of accumulation of ICP27, TK, VP16 and $U_L41$ mRNAs representative of viral α, β, $γ_1$ and $γ_2$ genes, respectively, and of the LAT and selected miRNAs. In the experiment shown, significant fluctuation in the levels of mRNAs was observed on day 3 but less so at later time points. In general, mRNAs attained peak levels on days 3 or 7 and decreased thereafter. The data indicate that the patterns of accumulation of mRNAs of wild-type virus were either similar or slightly elevated with respect to those of the recombinant viruses. In a similar vein, the patterns of accumulation of the LAT and miRNAs were either similar or slightly elevated with respect to the accumulation of the corresponding products of the recombinant viruses.

Interference with STAT3 Functions by a Virus Expressing a Gene Encoding a Dominant Negative STAT3

The following studies verified the STAT3 inhibitor studies that STAT3 plays a role in defining the status of latent virus and that interference with the function of STAT3 would lead to virus reactivation. For this experiment, trigeminal ganglia were excised 30 days after infection with wild-type virus or with the R128 or R130 recombinant viruses. One set of ganglia was immediately extracted and assayed for the amounts of viral DNA and mRNAs representing the major kinetic classes of viral genes. The remaining ganglia were incubated in medium containing antibody to NGF or both NGF+EGF for 24 hours and then assayed for the amounts of viral mRNAs, the LAT or representative miRNAs. The results were as follows:

The relative amounts of viral DNA recovered from trigeminal ganglia at the time of excision of the ganglia are shown in FIG. 6 Panel B. The results indicate that there was significantly less viral DNA in trigeminal ganglia of mice exposed to the recombinant virus carrying the Y705F substitution than in mice infected with wild-type virus. Conversely, trigeminal ganglia harboring the R128 recombinant viral genome expressing a wild-type STAT3 gene contained at least as much viral DNA as the ganglia carrying latent wild-type virus and significantly more than ganglia harboring latent R130 recombinant virus carrying the Y705F substitution.

FIG. 8 shows the relative amounts of mRNAs transcribed from representative genes sequentially derepressed during productive infection. Column 1 shows the basal levels of mRNA detected in ganglia processed immediately after excision. During the timeframe of a productive infection the amounts of viral transcripts increase approximately 50-fold on incubation in medium containing anti NGF antibody and approximately 2- to 3-fold in medium containing NGF+EGF. Consistent with the lower amount of viral DNA, fewer copies of viral mRNA were detected in ganglia harboring latent recombinant viruses (compare columns 4 and 7 with column 1). Comparison of columns 1-3 with 7-9 show that they exhibit similar patterns, indicating that in ganglia harboring R128 the pattern of activation of latent virus is similar to that of HSV-1(F). In contrast, ganglia harboring latent R130 exhibited higher levels of expression and accumulation of mRNAs in medium containing NGF+EGF than in medium containing antibody to NGF (compare columns 1-3 or 7-9 with 4-6).

Thus, the results of this study were congruent with those obtained with the STAT3 inhibitor and indicated that STAT3 defines the status of latent HSV-1 in murine trigeminal ganglia.

Induction of Reactivation of Latent HSV-1(F) by the STAT3 Inhibitor—in Contrast to the Induction of Reactivation by p300/CBP, Activation Requires De Novo Protein Synthesis The impetus for these studies was the observation that trigeminal ganglia harboring the R130 recombinant virus accumulated higher levels of viral mRNAs only on incubation in medium containing NGF+EGF, but not in medium containing antibody to NGF. One interpretation of the results was that the dominant negative STAT3 carrying the Y705F substitution had to perform or induce a function that was partly or totally blocked in ganglia incubated in medium containing antibody to NGF. To test the hypothesis that this function required de novo protein synthesis, ganglia excised 30 days after infection were incubated in medium containing NGF+EGF and the STAT3 inhibitor alone or inhibitor plus cycloheximide. As a control, duplicate ganglia harboring latent wild-type virus were incubated in medium containing inhibitory concentrations of TSA alone or both TSA and cycloheximide. The rationale in designing this study was based on the expectation that induction of reactivation by HDAC inhibitors would not require de novo protein synthesis.

The results, shown in FIG. 9, were as follows:

(1) The accumulation of mRNAs in ganglia exposed to TSA and cycloheximide (columns 2 and 3) were similar to those obtained in the absence of cycloheximide and 10-fold higher than those obtained in freshly excised ganglia (column 1). As expected from earlier studies, the amounts of the LAT and miRNAs were higher in cycloheximide-treated ganglia (column 8) than in those treated with TSA only (column 7).

(2) In contrast to the results of studies with the HDAC inhibitor, the levels of accumulated mRNAs were consistently lower in ganglia treated with both a STAT3 inhibitor and cycloheximide (Column 5) than with the inhibitor alone. In contrast, the levels of the LAT and miRNAs were higher in cycloheximide-treated ganglia.

(3) Thus, the induction of viral gene expression in latently infected ganglia by the inhibitor of STAT3 requires de novo protein synthesis. In contrast, activation of viral gene expression by an HDAC inhibitor does not require prior protein synthesis.

What is claimed:

1. A method of reducing latent virus in an individual, the method comprising:
   (i) administering a therapeutically effective amount of one or more agents to the individual that:
      (a) inhibits activity of signal transducer and activator of transcription 3 (STAT3), or
      (b) activates any of p300, CBP, or p300/CBP; wherein the one or more agents promotes reactivation of the latent virus, and
   (ii) administering a therapeutically effective amount of an antiviral agent to the individual, thereby reducing latent virus in the individual, wherein the latent virus is a herpes virus, a human cytomegalovirus, or a human immunodeficiency virus.

2. The method of claim 1, wherein the one or more agents that inhibits activity of STAT3 is selected from the group consisting of cucurbitacin I, niclosamide, cryptotanshinone, SD 1008, (S,E)-3-(6-Bromopyridin-2-yl)-2-cyano-N-(1-phenylethyl)acrylamide (Stat3 Inhibitor III), WP1066, Nifuroxazide, Stattic, S3I-201; 5,15-Diphenyl-21H,23H-porphine (Stat3 Inhibitor VIII), 5,15-DPP, 2-Hydroxy-4-(((4-methylphenyl)sulfonyloxy)acetyl)amino)-benzoic acid (NSC74859) and Kahweol.

3. The method of claim 2, wherein the one or more agents that activates any of p300, CBP, or p300/CBP is MSG I.

4. The method of any one of claims 1-3, further comprising administering a therapeutically effective amount of one or more HDAC inhibitory agents that inhibits the activity of a histone deacetylase (HDAC), wherein inhibition of the activity of the HDAC by the one or more HDAC inhibitory agents promotes reactivation of the virus.

5. The method of claim 4, wherein the one or more HDAC inhibitory agents is selected from the group consisting of sodium butyrate, vorinostatin (SAHA), valproic acid, trichostatin A (TSA), (3aR,6S,9S,12S)-9,12-Dibenzyl-6-[6-oxo-6-[(S)-oxiranyl]hexyl]-1,2,3,3a,8,9-hexahydro-5,8,11,13a-tetraaza-13aH-cyclopentacyclododecene-4,7,10,13(5H,6H,11H,12H)-tetrone (trapoxin B), phenylbutyrate, valproic acid, (2E)-N-Hydroxy-3-[3-(phenylsulfamoyl)phenyl]prop-2-enamide (belinostat PXD101), (2E)-N-hydroxy-3-[4-[[(2-hydroxyethyl)[2-(1H-indol-3-yl)ethyl]amino]methyl]phenyl]-2-propenamide (LAQ824), (2E)-N-hydroxy-3-[4-({[2-(2-methyl-1H-indol-3-yl)ethyl]amino}methyl)phenyl]acrylamide (panobinostat LBH589), Pyridin-3-ylmethyl N-[[4-[(2-aminophenyl)carbamoyl]phenyl]methyl]carbamate (entinostat, MS-275), 4-(Acetylamino)-N-(2-aminophenyl)benzamide (CI994), (E)-3-(4-((E)-3-(3-fluorophenyl)-3-oxoprop-1-enyl)-1-methyl-1H-pyrrol-2-yl)-N-hydroxyacrylamide (MC1568) and N-(2-Aminophenyl)-4-[[(4-pyridin-3-ylpyrimidin-2-yl)amino]methyl]benzamide (mocetinostat, MGCD0103).

6. A method of inhibiting reactivation of a virus in an individual, the method comprising:
   administering a therapeutically effective amount of one or more agents to the individual that:
      (a) activates signal transducer and activator of transcription 3 (STAT3), or
      (b) inhibits any of p300, CBP, or p300/CBP;
   wherein the one or more agents inhibits reactivation of the virus, and wherein the virus is a herpes virus, a human cytomegalovirus, or a human immunodeficiency virus.

7. The method of claim 6, wherein the one or more agents that activate STAT3 is selected from the group consisting of an interferon, epidermal growth factor, interleukin-5, interleukin-6, interleukin-10, hepatocyte growth factor, leukemia inhibitory factor, bone morphogenetic protein 2 and leptin.

8. The method of claim 7, wherein the one or more agents that inhibit any of p300, CBP, or p300/CBP is selected from the group consisting of 2-(3,4,5-Trihydroxyphenyl)chromenylium-3,5,7-triol (delphinidin), 4-[4-[[5-(4,5-Dimethyl-2-nitrophenyl)-2-furanyl]methylene]-4,5-dihydro-3-methyl-5-oxo-1H-pyrazol-1-yl]benzoic acid (C646), (1E,6E)-1,7-Bis(4-hydroxy-3-methoxyphenyl)hepta-1,6-diene-3,5-dione (curcumin), (1R,5R,7R)-3-(3,4-Dihydroxybenzoyl)-4-hydroxy-8,8-dimethyl-1,7-bis(3-methyl-2-buten-1-yl)-5-[(2S)-5-methyl-2-(1-methylethenyl)-4-hexen-1-yl]-Bicyclo[3.3.1]non-3-ene-2,9-dione (garcinol), and 2-Hydroxy-6-pentadecylbenzoic acid anacardic acid).

9. The method of any one of claims 6-8, further comprising administering a therapeutically effective amount of one or more HDAC activating agents that activates a histone deacetylase (HDAC), wherein activation of the HDAC by the one or more agents inhibits reactivation of the virus.

10. The method of claim 9, wherein the one or more HDAC activating agents is ITSA1 (N-(1H-Benzotriazol-1-yl)-2,4-dichlorobenzamide).

11. The method of claim 1, wherein the herpes virus is herpes simplex virus 1 (HSV-1) or herpes simplex virus 2 (HSV-2).

* * * * *

UNITED STATES PATENT AND TRADEMARK OFFICE
CERTIFICATE OF CORRECTION

PATENT NO. : 9,669,036 B2
APPLICATION NO. : 14/891200
DATED : June 6, 2017
INVENTOR(S) : Bernard Roizman et al.

Page 1 of 1

It is certified that error appears in the above-identified patent and that said Letters Patent is hereby corrected as shown below:

In the Claims

At Column 21, Line 22, "-4-(((4-" should be -- -4-((((4- --.

At Column 21, Line 41, "(belinostat PXD101)," should be -- (belinostat, PXD101), --.

At Column 21, Line 45, "(panobinostat LBH589)," should be -- (panobinostat, LBH589), --.

At Column 22, Line 34, "acid)." should be -- acid. --.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 1
ggtagtgctg ccccgttcct gaagaccaag ttc                                33

<210> SEQ ID NO 2
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 2
gaacttggtc ttcaggaacg gggcagcact acc                                33

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
cttaacagcg tcaacagcgt gccg                                          24

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ccaaagaggt gcgggagttt                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
agtgtgcggg gatgcagt                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
acgcgagagc cccacgta                                                 18
```